United States Patent
Torii et al.

(10) Patent No.: US 8,257,610 B2
(45) Date of Patent: Sep. 4, 2012

(54) WATER ABSORBING AGENT AND PRODUCTION METHOD THEREOF

(75) Inventors: Kazushi Torii, Hyogo (JP); Taishi Kobayashi, Hyogo (JP); Yoshifumi Adachi, Hyogo (JP); Yusuke Watanabe, Hyogo (JP); Toshimasa Kitayama, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 233 days.

(21) Appl. No.: 12/674,780

(22) PCT Filed: Sep. 26, 2008

(86) PCT No.: PCT/JP2008/067999
§ 371 (c)(1),
(2), (4) Date: Feb. 23, 2010

(87) PCT Pub. No.: WO2009/041731
PCT Pub. Date: Apr. 2, 2009

(65) Prior Publication Data
US 2011/0114881 A1    May 19, 2011

(30) Foreign Application Priority Data
Sep. 28, 2007   (JP) .................. 2007-256634

(51) Int. Cl.
*C09K 3/00*  (2006.01)
*C09K 3/32*  (2006.01)
*C09K 21/14* (2006.01)
*B01J 20/26* (2006.01)

(52) U.S. Cl. ........ 252/194; 252/184; 252/602; 252/603; 252/604; 252/610; 252/611; 502/402; 502/404

(58) Field of Classification Search .............. 252/194, 252/184, 8.05, 602, 603, 604, 606, 610, 611; 502/402, 404
See application file for complete search history.

(56) References Cited

U.S. PATENT DOCUMENTS

| | | | |
|---|---|---|---|
| 4,558,100 A * | 12/1985 | Kightlinger et al. | 525/329.1 |
| 5,886,124 A * | 3/1999 | Kightlinger et al. | 527/312 |
| 7,282,262 B2 * | 10/2007 | Adachi et al. | 428/402 |
| 2002/0128618 A1 | 9/2002 | Frenz et al. | |

(Continued)

FOREIGN PATENT DOCUMENTS
JP         63105064        5/1988
(Continued)

OTHER PUBLICATIONS

Chinese Office Action dated Jan. 31, 2012 in corresponding Chinese Application No. 200880108733.X.

*Primary Examiner* — Joseph D Anthony
(74) *Attorney, Agent, or Firm* — Roylance, Abrams, Berdo & Goodman, L.L.P.

(57) ABSTRACT

The present invention provides a water absorbing agent, and a method for producing the water absorbing agent. The water absorbing agent includes water absorbent resin particles, an organic acid and/or salt thereof having carbon number of 10 or more and not more than 30 in its molecule, and a water-soluble polyvalent cation. The method includes the step (i) of mixing the water absorbent resin particles, the organic acid and/or salt thereof having carbon number of 10 or more and not more than 30 in its molecule, and the water-soluble polyvalent cation with one another.

16 Claims, 1 Drawing Sheet

U.S. PATENT DOCUMENTS

| | | | |
|---|---|---|---|
| 2002/0165288 A1 | 11/2002 | Frenz et al. | |
| 2003/0020199 A1* | 1/2003 | Kajikawa et al. | 264/140 |
| 2003/0069359 A1 | 4/2003 | Torii et al. | |
| 2004/0071966 A1 | 4/2004 | Inger et al. | |
| 2005/0020780 A1 | 1/2005 | Inger et al. | |
| 2005/0118423 A1* | 6/2005 | Adachi et al. | 428/402 |
| 2005/0245684 A1 | 11/2005 | Daniel et al. | |
| 2006/0204755 A1* | 9/2006 | Torii et al. | 428/402 |
| 2006/0229413 A1 | 10/2006 | Torii et al. | |
| 2008/0032888 A1* | 2/2008 | Nakamura et al. | 502/402 |
| 2011/0114881 A1* | 5/2011 | Torii et al. | 252/194 |

FOREIGN PATENT DOCUMENTS

| | | |
|---|---|---|
| JP | 6080889 | 3/1994 |
| JP | 6345980 | 12/1994 |
| WO | 2004069915 | 8/2004 |

* cited by examiner

WATER ABSORBING AGENT AND PRODUCTION METHOD THEREOF

TECHNICAL FIELD

The present invention relates to a water absorbing agent and a method of producing the same, particularly, a water absorbing agent that is suitable for use in a sanitary material such as a disposable diaper, a sanitary napkin, and an incontinence pad, for example, and a method of producing the water absorbing agent.

BACKGROUND ART

Conventionally, a water absorbing material made of a hydrophilic fiber such as pulp, and a water absorbing agent has been in widespread use in sanitary materials such as a disposable diaper, a sanitary napkin, and an incontinence pad, for the purpose of absorbing body fluids.

For enhancement in convenience, it has been demanded to make these sanitary materials thinner in recent years. This results in that, in a water absorbing material, a ratio of the hydrophilic fiber having low bulk specific gravity is decreased, and a ratio of the water absorbing agent having a high water absorbing rate and high bulk specific gravity is increased. Water absorbing agent usage in the water absorbing material is thus increased so as to make the sanitary material thinner without a reduction in its properties such as a water absorption amount.

Such a sanitary material having a small ratio of the hydrophilic fiber and a large ratio of the water absorbing agent is preferable for merely keeping liquid. However, when actually used in a disposable diaper, for example, such a sanitary material has a problem in distribution and diffusion of the liquid. For example, a large amount of the water absorbing agent turns into a soft gel state when absorbing water, and causes a gel blocking phenomenon in which water is prevented from being absorbed deeper into the water absorbing agent. This dramatically decreases a diffusing property of the liquid in the sanitary material. The ratio of the hydrophilic fiber to the water absorbing agent is inevitably limited so as to both avoid such a problem and maintain absorption characteristics of the water absorbing material. As a result, the sanitary material cannot be thinner than a certain limit.

In order to both suppress the gel blocking and realize a sufficient absorption amount, it is necessary to obtain a water absorbing agent that is excellent in a balance between an absorption capacity represented by a centrifugal retention capacity (CRC), for example, and liquid permeability represented by a saline flow conductivity (SFC), for example. However, they have such a relationship that an increase in one results in a decrease in the other. This makes it difficult to improve the relationship (balance) between them to a successful level. As means for attaining such an object, the following techniques have been known, for example.

Patent Document 1 discloses a water absorbent resin that has been processed with a tri- or more-valent cation. Patent Document 2 discloses a technique with which an electrostatic or stereoscopic spacer is used with a water absorbent resin. Patent Document 3 discloses a particulate water absorbing agent containing: water absorbent resin particles produced by (i) cross-linking a monomer containing acrylic acid and/or salt thereof, and (ii) further cross-linking a surface of each of particles thus obtained, which particles have been pulverized into irregular shapes; and an agent for enhancing liquid permeability. Thereby, Patent Document 3 provides a water absorbing agent having properties of both capillary suction pressure and liquid permeability.

Meanwhile, other than Patent Documents 1 through 3 whose object is to improve the balance between the absorption capacity and the liquid permeability, there has been proposed to mix various additives for the purpose of an improvement in various properties of a water absorbent resin.

For example, Patent Document 4 proposes a water absorbing agent composition made from a water absorbent resin, and an anionic surfactant having a carboxyl group or salt thereof. Thereby, Patent Document 4 provides a salt-tolerant water absorbing agent composition having excellent absorption performance with respect to a saline solution.

Further, Patent Document 5 proposes a particulate water absorbing agent containing: a particulate water absorbent resin having a surface-cross-linking structure; and polyvalent metal salt of organic acid having 7 or more carbon atoms in its molecule. Thereby, Patent Document 5 provides a particulate water absorbing agent having stable and excellent absorption performance, the particulate water absorbing agent: being advantageous in powder flowability when absorbing moisture, and under a dry condition where a moisture content is 0 mass % to 20 mass %; being excellent in handling during transportation etc.; and, being so tolerant to a mechanical impact in producing and carrying the particulate water absorbing agent, and manufacturing a water absorbing good with the water absorbing agent. The particulate water absorbing agent so tolerant to such a mechanical impact that the mechanical impact hardly reduces (i) absorption performance, and (ii) flowability when absorbing moisture.

Furthermore, Patent Document 6 discloses a high water-absorption resin composition produced by compounding high water-absorption resin powder of 100 pts.wt. with stearic acid of 0.1 pts.wt. to 5 pts.wt and inorganic powder of 0.1 pts.wt to 1 pts.wt. Thereby, Patent Document 6 provides a high water-absorption resin composition that not only improves absorption characteristics (a fish eye formation avoidability, dispersibility, an absorption speed, and absorption performance) and powder flowability but also has a dust formation avoidability.

Moreover, Patent Document 7 proposes a method of producing a water absorbing agent, including the step of mixing: water absorbent resin particles having an internal cross-linking structure that is obtained by polymerizing a water-soluble unsaturated monomer; organic acid (salt) having a low carbon number; and water-soluble polyvalent metal salt. Thereby, Patent Document 7 provides a method of producing a water absorbing agent by mixing water absorbent resin particles and a metal compound, wherein: it is possible to (i) suppress penetration of metal composition into the water absorbent resin particles, and (ii) realize high liquid permeability and uniform properties.

Further, Patent Document 8 proposes a method of producing a water absorbing agent, including the step of: mixing water absorbent resin particles and a cationic polymer compound in which a specific region is crosslinked. Thereby, Patent Document 8 provides a water absorbent resin that is excellent in an absorbency against pressure (AAP), a gel layer's flow rate under pressure (FRUP), and a saline flow conductivity (SFC), and can keep these effects for a long period.

[Patent Document 1]
Pamphlet of International Publication WO2001/74913 (published on Oct. 11, 2001)
[Patent Document 2]]]
Specification of US Patent Application Publication No. 2002/0128618 (published on Sep. 12, 2002

[Patent Document 3]
Pamphlet of International Publication WO2004/069915 (published on Aug. 19, 2004)
[Patent Document 4]
Japanese Unexamined Patent Publication No. Tokukaihei 6-345980 (published on Dec. 20, 1994)
[Patent Document 5]
Japanese Unexamined Patent Publication Tokukai 2004-261796 (published on Sep. 24, 2004]
[Patent Document 6)
Japanese Unexamined Patent Publication Tokukaisho 63-105064 (published on May 10, 1988)
[Patent Document 7]
Japanese Unexamined Patent Publication Tokukai 2005-344103 (published on Dec. 15, 2005)
[Patent Document 8]
Japanese Unexamined Patent Publication Tokukai 2003-62460 (published on Mar. 4, 2003)

DISCLOSURE OF INVENTION

Problem to be Solved by the Invention

The techniques disclosed in Patent Documents 1 through 3 are techniques for accomplishing an improvement in the balance between the absorption capacity and the liquid permeability by adding an additive having an effect of increasing the liquid permeability, such as polyvalent metal salt (metal cation), inorganic particles, or a polycation. However, the relationship (balance) has still not reached a sufficient level, and much improvement has been demanded. Further, the techniques disclosed in Patent Documents 4 through 8 have not taken the relationship (balance) between the absorption capacity and the liquid permeability to the sufficient level.

Specifically, it is demanded for the water absorbing agent to have both a centrifugal retention capacity (CRC) and a saline flow conductivity (SFC) when the water absorbing agent is actually used. However, the conventional techniques have not successfully satisfied these properties.

The present invention is made in view of the problem. An object of the present invention is to provide: a water absorbing agent that is excellent in a balance between the centrifugal retention capacity (CRC) and the saline flow conductivity (SFC); and a method of producing the water absorbing agent.

Means to Solve the Problems

The inventors of the present invention diligently studied the foregoing problems. As a result, they arranged a water absorbing agent, including water absorbent resin particles; an organic acid and/or salt thereof having carbon number of 10 or more and not more than 30 in its molecule; and a water-soluble polyvalent cation, more specifically a water absorbing agent so that organic acid whose carbon number is 10 or more and not more than 30 in its molecule and/or salt thereof and water-soluble polyvalent cation exist on a surface of each of the water absorbent resin particles. They found that, in this case, the water absorbing agent is much more excellent in a balance between a centrifugal retention capacity (CRC) and a saline flow conductivity (SFC) than water absorbing agents obtained by conventional techniques. In this way, they completed the present invention.

In order to solve the foregoing problems, a water absorbing agent according to the present invention is a water absorbing agent, comprising: water absorbent resin particles; an organic acid and/or salt thereof having carbon number of 10 or more and not more than 30 in its molecule; and a water-soluble polyvalent cation.

It is preferable in the water absorbing agent according to the present invention that the organic acid and/or salt thereof having carbon number of 10 or more and not more than 30 in its molecule, and the water-soluble polyvalent cation exist on a surface of each of the water absorbent resin particles.

It is preferable in the water absorbing agent according to the present invention that the organic acid and/or salt thereof has a hydrocarbon chain having carbon number of 9 or more in its molecule.

It is preferable to arrange the water absorbing agent according to the present invention so that the surface of the water absorbent resin particle is crosslinked.

It is preferable to arrange the water absorbing agent according to the present invention so that an amount of the organic acid and/or salt thereof ranges from 0.0001 to 5 mass % relative to an entire amount of the water absorbing agent.

It is preferable to arrange the water absorbing agent according to the present invention so that an amount of the water-soluble polyvalent cation ranges from 0.001 to 5 mass % relative to an entire amount of the water absorbing agent.

It is preferable to arrange the water absorbing agent according to the present invention so that the organic acid and/or salt thereof is a compound containing a carboxyl group.

It is preferable to arrange the water absorbing agent according to the present invention so that the salt is made of organic acid and univalent cation.

It is preferable to arrange the water absorbing agent according to the present invention so that the water-soluble polyvalent cation is water-soluble polyvalent metal salt.

It is preferable to arrange the water absorbing agent according to the present invention so that the water-soluble polyvalent cation is a water-soluble cationic polymer compound.

In order to solve the foregoing problems, a method according to the present invention is a method for producing a water absorbing agent including water absorbent resin particles, an organic acid and/or salt thereof having carbon number of 10 or more and not more than 30 in its molecule, and a water-soluble polyvalent cation, said method comprising the step (i) of mixing the water absorbent resin particles, the organic acid and/or salt thereof having carbon number of 10 or more and not more than 30 in its molecule, and the water-soluble polyvalent cation with one another.

A method according to the present invention may be a method for producing a water absorbing agent including water absorbent resin particles, wherein organic acid whose carbon number is 10 or more and not more than 30 in its molecule and/or salt thereof and water-soluble polyvalent cation exist on a surface of each of the water absorbent resin particles, said method comprising the step (i) of mixing the water absorbent resin particles, the organic acid whose carbon number is 10 or more and not more than 30 in its molecule and/or salt thereof, and the water-soluble polyvalent cation with one another.

It is preferable to arrange the method according to the present invention for producing a water absorbing agent so as to further include the step (ii) of cross-linking a surface of each of the water absorbent resin particles with a surface cross-linking agent.

It is preferable to arrange the method according to the present invention for producing a water absorbing agent so that the step (i) is carried out during the step (ii) and/or after the step (ii).

It is preferable to arrange the method according to the present invention for producing a water absorbing agent so that the step (i) is such that the organic acid and/or salt thereof having carbon number of 10 or more and not more than 30 in its molecule is mixed with the water absorbent resin particles at the same time as or before addition of the water-soluble polyvalent cation.

It is preferable to arrange the method according to the present invention for producing a water absorbing agent so that a solution, an emulsification solution, or a suspension solution of the organic acid and/or salt thereof having carbon number of 10 or more and not more than 30 in its molecule is mixed with the water absorbent resin particles.

It is preferable to arrange the method according to the present invention for producing a water absorbing agent so that an aqueous solution of the water-soluble polyvalent cation is mixed in.

EFFECTS OF THE INVENTION

As described above, a water absorbing agent according to the present invention is a water absorbing agent, comprising: water absorbent resin particles; an organic acid and/or salt thereof having carbon number of 10 or more and not more than 30 in its molecule; and a water-soluble polyvalent cation, more specifically, a water absorbing agent including water absorbent resin particles, wherein organic acid whose carbon number is 10 or more and not more than 30 in its molecule and/or salt thereof and water-soluble polyvalent cation exist on a surface of each of the water absorbent resin particles. Thus, it is possible to provide (i) a water absorbing agent which is excellent in a balance between a centrifugal retention capacity (CRC) and a saline flow conductivity (SFC) and (ii) a method for producing the water absorbing agent. Further, the present invention allows for production of water absorbent resin particles which is excellent in a balance between a centrifugal retention capacity (CRC) indicative of an absorption capacity of the water absorbing agent and a saline flow conductivity (SFC) indicative of liquid permeability, so that it is possible to provide (I) a water absorbing agent which allows an absorbent core to absorb liquid quickly and (II) a method for producing the water absorbing agent.

For a fuller understanding of the nature and advantages of the invention, reference should be made to the ensuing detailed description taken in conjunction with the accompanying drawings.

EXPLANATION OF REFERENCE NUMERALS

Figure 1:
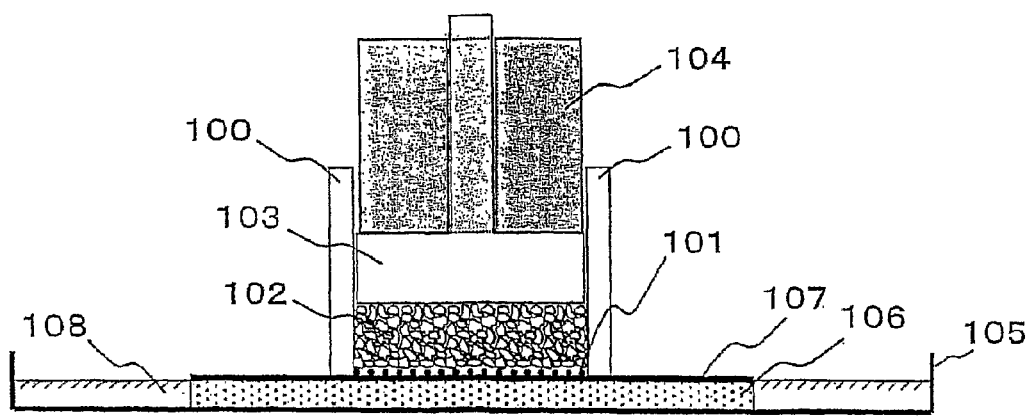
FIG. 1 is a schematic view illustrating a measuring apparatus of AAP, which was used in Examples.

31: Tank
32: Glass tube
33: 0.69 wt % saline
34: L-shaped Tube with cock
35: Cock
40: Vessel
41: Cell
42: Stainless metal net
43: Stainless metal net
44: Swelling gel
45: Glass filter
46: Piston
47: Hole of piston
48: Collecting vessel
49: Pan scales
100: Plastic supporting cylinder
101: Stainless metal net (400 mesh)
102: Swelling gel
103: Piston
104: Load (weight)
105: Petri dish
106: Glass filter
107: Filter paper
108: 0.9 wt % saline

BEST MODE FOR CARRYING OUT THE INVENTION

The following description explains the present embodiment. However, the scope of the present invention is not limited to this description, but rather may be applied in many variations within the spirit of the present invention. In the present invention, "weight" and "mass", and "weight %" and "mass %" are regarded having the same meaning; the expression used in the description is unified as "mass" and "mass %".

The following are definitions of abbreviations used in this description. In the present specification, a CRC (Centrifuge Retention Capacity) is a centrifuge retention capacity, and is a value obtained by a measuring method as explained in Examples later described. An SFC (Saline Flow Conductivity) is a conductivity of a saline flow, and is a value obtained by a measuring method as explained in Examples later described. An AAP (Absorbency against Pressure) is absorbency under a pressure of 4.83 kPa, and is a value obtained by a measuring method as explained in Examples later described. A D50 (Distribution) is a mass median particle size, and is a value obtained by a measuring method explained in Examples later described. A $\sigma\xi$ is a logarithmic standard deviation of a particle size distribution, and is a value obtained by a measuring method explained in Examples later described. Moreover, in the present specification, saline denotes sodium chloride aqueous solution (0.9 mass %).

A water absorbing agent according to the present invention is an absorbing solidification agent of an aqueous liquid which absorbing solidification agent contains water absorbing resin particles, and further contains an organic acid and/or salt thereof having carbon number of 10 or more and not more than 30 in its molecule and water-soluble polyvalent cation.

The water absorbing agent according to the present invention is sufficient as long as the water absorbing agent contains water absorbing resin particles as its main component, and further contains the organic acid and/or salt thereof having carbon number of 10 or more and not more than 30 in its molecule and the water-soluble polyvalent cation. Therefore, in the present invention, the water absorbing agent may be one whose main component is the water absorbing resin particles, further containing the organic acid and/or salt thereof having carbon number of 10 or more and not more than 30 in its molecule and the water-soluble polyvalent cation, and if necessary, contains a small amount of additives and/or water. The "main component" indicates that an amount of the water absorbing resin particles contained in the water absorbing agent is at least 50 mass % relative the entire water absorbing agent. The amount of the water absorbing resin particles contained in the water absorbing agent relative to the entire water absorbing agent is preferably in a range of not less than 60 mass % but not more than 99.999 mass %, more preferably in a range of not less than 80 mass % but not more than 99.999 mass %, further preferably in a range of not less than 90 mass % but not more than 99.999 mass %, particularly preferably in a range of not less than 95 mass % but not more than 99.999 mass %, and is most preferred in a range of not less than 98 mass % but not more than 99.999 mass %.

An amount of the organic acid and/or salt thereof having carbon number of 10 or more and not more than 30 in its molecule contained relative to the entire water absorbing agent, is preferably in a range of not less than 0.0001 mass % but not more than 5 mass %, more preferably not less than 0.0005 mass % but not more than 5 mass %, further preferably not less than 0.001 mass % but not more than 5 mass %, especially preferably not less than 0.005 mass % but not more than 3 mass %, and most preferably not less than 0.01 mass % but not more than 1 mass %.

The water absorbing agent preferably contains not less than 0.0001 mass % of the organic salt relative to the entire water absorbing agent, so as to obtain a water absorbing agent having an excellent balance in the centrifuge retention capacity (CRC) and the saline flow conductivity (SFC). Moreover, the water absorbing agent preferably contains not more than 5 mass % of the organic salt relative to the entire water absorbing agent, since an improvement in SFC is expectable corresponding to the added amount.

An amount contained of the water-soluble polyvalent cation relative to the entire water absorbing resin is preferably in a range of not less than 0.001 mass % but not more than 5 mass %, more preferably in a range of not less than 0.005 mass % but not more than 3 mass %, and further preferably in a range of not less than 0.01 mass % but not more than 1 mass %.

The water absorbing agent preferably contains at least 0.001 mass % of the water-soluble polyvalent cation relative to the entire water absorbing agent, so as to obtain a water absorbing agent having an excellent balance in the centrifuge retention capacity (CRC) and the saline flow conductivity (SFC). Moreover, the water absorbing agent preferably contains not more than 5 mass % of water-soluble polyvalent cation relative to the entire water absorbing agent, since an improvement in SFC is expectable corresponding to the added amount.

Other than the water absorbing resin particles and organic acid and/or salt thereof having carbon number of 10 or more and not more than 30 in its molecule and the water-soluble polyvalent cation, water is a main component of the water absorbing agent according to the present invention, and a small amount of other additives are used if necessary.

The water absorbing agent is an absorbing solidification agent of an aqueous liquid. The aqueous liquid is not limited to water, and is not particularly limited as long as the aqueous liquid contains water, for example urine, blood, excrement, waste fluid, moisture and vapor, ice, a mixture of water and an organic solvent and/or an inorganic solvent, rainwater, ground water, and the like. However, urine, particularly urine of human beings is preferred.

The following description sequentially explains (1) water absorbing resin particles contained in water absorbing agent of the present invention, (2) organic acid and/or salt thereof having carbon number of 10 or more and not more than 30 in its molecule, (3) water-soluble polyvalent cation, (4) water absorbing agent, (5) method for producing a water absorbing agent, and (6) absorbing material.

(1) Water Absorbing Resin Particles Contained in Water Absorbing Agent of Present Invention Water absorbing resin particles to be used in the water absorbing agent according to the present invention are particles of a water-insoluble water-swelling hydrogel-forming polymer (hereinafter the water absorbing resin may be referred to as water-insoluble water-swelling hydrogel-forming polymer in the present specification), which is obtainable by polymerizing a water-soluble unsaturated monomer.

Specific examples of the water-insoluble water-swelling hydrogel-forming polymer encompass: a partially neutralized, cross-linked polyacrylic acid polymer (e.g., U.S. Pat. Nos. 4,625,001, 4,654,039, 5,250,640, and 5,275,773, and European patent No. 456136), a cross-linked and partially neutralized starch-acrylic acid-grafted polymer (U.S. Pat. No. 4,076,663), an isobutylene-maleic copolymer (U.S. Pat. No. 4,389,513), a saponified vinyl acetate-acrylic acid copolymer (U.S. Pat. No. 4,124,748), a hydrolysate of acrylamide (co)polymer (U.S. Pat. No. 3,959,569), and a hydrolysate of acrylonitrile polymer (U.S. Pat. No. 3,935,099).

The water absorbing resin particles contained in the water absorbing agent of the present invention are preferably particles of water absorbing resin made of a polyacrylic acid (salt) cross-linked polymer obtained by polymerizing a monomer containing acrylic acid and/or salt thereof, as the water-soluble unsaturated monomer. The polyacrylic acid (salt) cross-linked polymer denotes a cross-linked polymer obtained by polymerizing a monomer containing at least 50 mol %, preferably not less than 70 mol %, more preferably not less than 90 mol % of acrylic acid and/or the salt thereof.

Moreover, at least 50 mol % but not more than 90 mol %, more preferably not less than 60 mol % but not more than 80 mol % of an acid group of the polyacrylic acid (salt) cross-linked polymer is preferably neutralized. Examples of the polyacrylic acid salt encompass: alkaline metal salts such as sodium, potassium, and lithium; ammonium salt; and amine salt. Among these, it is preferable for the polyacrylic acid salt to be sodium salt. Neutralization in order to form the salt may be carried out in the monomer state prior to the polymerization, or may be carried out in a polymer state during the polymerization or after the polymerization. Alternatively, the neutralization may be carried out in both states.

The polyacrylic acid (salt) cross-linking polymer that is preferably used as the water absorbing resin particles used in the water absorbing agent according to the present invention may be one which another monomer is copolymerized with the monomer used as the main component (acrylic acid and/or the salt thereof) if necessary.

Examples of the another monomer encompass: anionic unsaturated monomers and salts thereof such as methacrylic acid, maleic acid, vinyl sulfonic acid, styrene sulfonic acid, 2-(meth)acrylamide-2-methylpropane sulfonic acid, 2-(meth)acryloylethane sulfonic acid, and 2-(meth)acryloylpropane sulfonic acid; nonionic unsaturated monomers containing a hydrophilic group, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl(meth)acrylate, methoxy polyethylene glycol(meth)acyrlate, polyethylene glycol mono(meth)acyrlate, vinylpyridine, N-vinylpyrrolidon, N-acryloyl piperidine, N-acryloyl pyrrolidine, and N-vinyl acetamide; and cationic unsaturated monomers such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and quaternary salts thereof. A using amount of the other monomer is preferably in a range of not less than 0 mol % but not more than 30 mol % relative to an entire monomer, and is more preferably in a range of not less than 0 mol % but not more than 10 mol %.

It is preferable for the water absorbing resin particles that are used in the present invention to be a cross-linked polymer having an internal cross-linked structure. The following methods are examples of a method for introducing the internal cross-linked structure to the water absorbing resin particles: a method introducing the internal cross-linked structure by self-cross-linking without use of a cross-linking agent; a method introducing the internal cross-linked structure by copolymerizing or reacting with an internal cross-linking agent having at least two polymerized unsaturated groups and/or at least two reactive groups in one molecule; and the like. Among these methods, it is preferable to use the method introducing the internal cross-linked structure by copolymerizing or reacting with the internal cross-linking agent.

Specific examples of the internal cross-linking agent encompass: N,N'-methylene bis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerol tri(meth)acrylate, glycerol acrylate methacrylate, ethylene oxide denatured trimethylolpropane tri(meth)acrylate, pentaerythritol tetra(meth)acrylate, dipentaerythritol hexa(meth)acrylate, triallylcyanurate, triallylisocyanurate, triallylphosphate, triallylamine, poly(meth)allyoxyalkane, (poly)ethylene glycol diglycidyl ether, glycerol diglycidyl ether; polyalcohols such as ethylene glycol, polyethylene glycol, 1,4-butanediol, propylene glycol, glycerin, and pentaerythritol; ethylenediamine, polyethyleneimine, and glycidyl(meth)acrylate.

One type or two or more types of the internal cross-linking agents may be used. In particular, it is preferable to essentially use, as the internal cross-linking agent, a compound having at least two polymerized unsaturated groups, in view of water absorbing characteristics of the water absorbing resin particles thus obtained.

A using amount of the internal cross-linking agent is preferably in a range of not less than 0.005 mol % but not more than 3 mol % relative to the entire monomer, and is further preferably in a range of not less than 0.01 mol % but not more than 1.5 mol %, and is most preferred in a range of not less than 0.05 mol % but not more than 0.2 mol %.

In polymerization, a hydrophilic polymer or chain transfer agent may be added. Examples of the hydrophilic polymer encompass: hydrophilic polymers such as starch-cellulose, a derivative of starch-cellulose, polyvinyl alcohol, polyacrylic acid and salts thereof, and a cross-linked polymer of polyacrylic acid and salts thereof. Examples of the chain transfer agent encompass hypophosphorous acid and salts thereof.

In polymerizing a monomer whose main component is the acrylic acid and/or the salt thereof, bulk polymerization, reversed phase suspension polymerization, or precipitation polymerization may be carried out. However, from views of functions and ease in controlling the polymerization, it is more preferable to carry out aqueous solution polymerization, in which the monomer is made into an aqueous solution. Such polymerization method is described, for example, in U.S. Pat. Nos. 4,625,001, 4,769,427, 4,873,299, 4,093,776, 4,367,323, 4,446,261, 4,683,274, 4,690,996, 4,721,647, 4,738,867, and 4,748,076, and in U.S. patent application publication No. 2002/40095.

In the polymerization, radical polymerization initiators such as potassium persulfate, ammonium persulfate, sodium persulfate, t-butyl hydroperoxide, hydrogen peroxide, and 2,2-azobis(2-amidinopropane)dihydrochloride, and activated energy rays such as ultraviolet rays and electron beams may be used. In a case where the radical polymerization initiator is used, a reducing agent such as sodium sulfite, sodium bisulfite, ferrous sulfate, and L-ascorbic acid may be used together with the radical polymerization initiator, so as to carry out a redox polymerization. A using amount of the polymerization initiator is preferably in a range of not less than 0.001 mol % but not more than 2 mol % relative to the entire monomer, and is more preferably in a range of not less than 0.01 mol % but not more than 0.5 mol %.

A shape of the water absorbing resin particles thus obtained by the polymerization is generally an irregularly-pulverized shape, a sphere shape, a fiber shape, a bar shape, a substantially sphere shape, a flat shape, or the like. However, it is preferable for the shape of the water absorbing resin particles to be the irregularly-pulverized shape. The water absorbing resin particles in the irregularly-pulverized shape allows effective presence of the organic acid and/or salt thereof having carbon number of 10 or more and not more than 30 in its molecule on a surface of the water absorbing resin particles.

In a case where the cross-linked polymer is obtained by the aqueous polymerization and is of a gel form, in other words, the cross-linked polymer is a hydrous gel cross-linked polymer (hereinafter may be referred to as hydrous gel), the hydrous gel cross-linked polymer is dried, and is usually pulverized before and/or after drying so as to obtain the water absorbing resin particles. In the present invention, drying denotes an operation to increase solid content. Usually, the solid content is to increase as compared to that of which is not dried, however is more preferably increased so that the solid content increases to at least 90 mass %, and having an upper limit of approximately 99 mass %. The drying may be carried out concurrently with the polymerization, or both the drying during the polymerization and the drying after the polymerization may be carried out. However, it is preferable to provide a drying step after the polymerization, for drying the hydrous gel cross-linked polymer by use of a drying device. In the present invention, it is preferable to dry the water absorbing resin to the solid content of at least 90 mass %, and further preferably to not less than 95 mass %. Low solid content not only worsens fluidity of the water absorbing resin, which causes difficulty in production, but also makes it difficult to pulverize the water absorbing resin. This may cause loss in control of producing a specific particle size distribution. Note that the solid content of the water absorbing resin is indicative of a value to be measured by a measuring method later described.

In the present invention, the drying is carried out in a temperature range of 100° C. to 250° C., for at least 50% of an entire time of the drying step, and preferably during the entire drying step. A temperature less than 100° C. causes undried products to occur, which not only effects pulverizing of the water absorbing resin particles, but also makes it difficult to control the particle size distribution. A drying temperature of not less than 250° C. causes damage to the water absorbing resin. This damage causes an increase in water-soluble content of the water absorbing resin. As a result, an improvement of physical properties may not be attained. Drying temperature is defined by a heat carrier, however if it is not possible to define the drying temperature by the heat carrier, for example in a case of a microwave, the drying temperature is defined by material temperature. A drying method is not particularly limited as long as the drying temperature is in the above range, and methods such as hot air drying, no-wind drying, vacuum drying, infrared ray drying, or microwave drying are suitably used. In particular, it is preferable to use the hot air drying method. A drying airflow in a case where the hot air drying is used is preferably in a range of 0.01 m/sec to 10 m/sec, and is more preferably in a range of 0.1 m/sec to 5 m/sec.

The drying temperature is preferably in a range of 130° C. to 220° C., and is further preferably in a range of 150° C. to 200° C. The drying may be carried out at a fixed temperature or at varying temperatures, however is preferable so that the entire drying step is carried out in the above temperature range, effectively.

A drying time differs depending on a surface area and moisture content of the polymer and a type of drying machine, and is appropriately selected so that the polymer attains a target moisture content. The drying time is usually in a range of 10 to 120 minutes, more preferably in a range of 20 to 90 minutes, and further preferably in a range of 30 to 60 minutes. If the drying time is less than 10 minutes, changes which occur in the polymer chain internal of the water absorbing resin particles are small. With such small change, a sufficient improvement effect is unlikely to be attained. As a result, an improvement of the physical properties may not be attained. In comparison, the drying time of 120 minutes or longer causes the water absorbing resin to be damaged. As a result, the amount of the water-soluble content increases, thereby failing to improve the physical properties.

The water absorbing resin thus obtained is crushed by a crushing machine. Crushing may be carried out at any timing, before the drying, during the drying, or after the drying, however it is preferably carried out after the drying. The crushing machine is not particularly limited, and a roller-type crushing machine (e.g. roller mill), a hammer type crushing machine (e.g. hammer mill), an impact mill, a cutter mill, a turbo grinder, a ball mill, a flash mill or the like is used for example. In particular, it is preferable to use the roller mill in order to control the particle size distribution. It is more preferable to crush the water absorbing resin for at least two times consecutively in order to control the particle size distribution, and is further preferable to crush the water absorbing resin for at least three times consecutively. In the case where the water absorbing resin is crushed for at least two times, the crushing machine thus used may be same or different to each other. It is also possible to use different types of crushing machines combined.

In order to control the water absorbing resin particles thus crushed in a specific particle size distribution, the water absorbing resin particles may be classified by use of a sieve having a specific mesh size. A classifying machine that is used for classifying the water absorbing resin particles by use of the sieve is not particularly limited. For example, a vibrating sieve (i.e., an unbalanced weight-driven method, a resonant method, a vibrating motor method, an electromagnetic method, and a circular vibration method), in-plane motion sieve (i.e., a horizontal motion method, a horizontal circle-linear motion method, and a three-dimensional motion method), a movable net sieve, a compulsory stirring sieve, a net plane vibration sieve, a wind force sieve, a sonic sieve, and the like are used. Among these methods, the vibrating sieve or the in-plane motion sieve is preferably used. The opening of the sieve is preferably in a range of 1000 μm to 300 μm, more preferably in a range of 900 μm to 400 μm, and further preferably in a range of 710 μm to 450 μm. The target particle size distribution may not be attained if the opening is of a size not within this range.

In order to control the water absorbing resin particles thus classified as the above into a further specific particle size distribution, the water absorbing resin particles may be further classified, so as to remove a part or all of the particles that are smaller than the specific particle size. A classifying machine to be used in such step is not particularly limited, however the aforementioned machines are preferably used, and other machines such as a pulverizing type classification device (e.g., centrifugal force type, ineritial force type) may also be used. In the present step, a part or all of the particles having a particle size of less than 200 μm, more preferably less than 150 μm, and most preferably less than 106 μm, is to be removed.

The water absorbing resin particles used in the present invention is more preferably surface cross-linked with an organic surface cross-linking agent and/or a water-soluble inorganic surface cross-linking agent, each of which is a surface cross-linking agent, on a shallow surface of the water absorbing resin particles. The water absorbing resin particles whose shallow surface is surface cross-linked by the surface cross-linking agent, which water absorbing resin are contained in the water absorbing agent, allows reduction of rewet occurring when pressure is given on a swollen water absorbing agent. Therefore, an AAP, in other words, absorbency against pressure, is improved.

The surface cross-linking by use of the surface cross-linking agent may be carried out at any stage of production, however is preferably carried out after the water absorbing resin particles are controlled to a specific particle size distribution.

An example of the surface cross-linking agent usable for the surface cross-linking process includes an organic surface cross-linking agent and/or a water-soluble inorganic surface cross-linking agent which contains at least two functional groups that can react with a functional group contained in the water absorbing resin particles, for example a carboxyl group. Such surface cross-linking agent may be organic or inorganic, however in particular, the water-soluble organic surface cross-linking agent is suitably used.

Examples of the surface cross-linking agent encompass: polyalcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerol, 2-butene-1,4-diol, 1,3-butanediol, 1,4-butanediol, 1,5-pentanediol, 1,6-hexanediol, 1,2-cyclohexandimethanol, 1,2-cyclohexanol, trimethylolpropane, diethanolamine, triethanolamine, polyoxypropylene, oxyethylene-oxypropylene block copolymer, pentaerythritol, and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyvalent amine compounds such as ethylenediamine, diethylenetriamine, triethylenetetramine, tetraethylenepentamine, pentaethylenehexamine, and polyethyleneimine, and its inorganic or organic salt (for example, azetidinium salt and the like); polyvalent isocyanate compounds such as 2,4-tolylene diisocyanate and hexamethylene diisocyanate; polyvalent oxazoline compounds such as 1,2-ethylene bisoxazoline; carbonic acid derivatives such as urea, thiourea, guanidine, dicyandiamide, and 2-oxazolidinone; alkylene carbonate compounds such as 1,3-dioxolane-2-one, 4-methyl-1,3-dioxolane-2-on, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds and its polyvalent amine additives (for example "Kymene" produced by Hercules Inc.: Registered Trademark) such as epichlorohydrin, epibromhydrin, and α-methylepichlorohydrin; silane coupling agents such as γ-glycidoxypropyltrimethoxysilane, and γ-aminopropyltriethoxysilane; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, 3-butyl-3-oxetaneethanol, 3-chloromethyl-3-methyloxetane, 3-chloromethyl-3-ethyloxetane, and polyvalent oxetane compounds.

One type of the surface cross-linking agent may be used, or two or more types of the surface cross-linking agent may be used combined. In particular, the polyalcohols are preferred for their high safeness and improvement in hydrophilicity of the surface of the water absorbing resin particles.

A using amount of the surface cross-linking agent is preferably in a range of not less than 0.001 parts by mass but not more than 5 parts by mass, relative to 100 parts by mass of solid content of the water absorbing resin particles.

Water may be used in mixing the surface cross-linking agent and the water absorbing resin particles. A using amount of the water is preferably in a range of more than 0.5 parts by mass but not more than 10 parts by mass relative to 100 parts by mass of the solid content of the water absorbing resin particles, and is more preferably in a range of not less than 1 parts by mass but not more than 5 parts by mass.

When the surface cross-linking agent or an aqueous solution thereof is mixed with the water absorbing resin particles, a hydrophilic organic solvent or a third material may be used as a mixing auxiliary agent. In a case where the hydrophilic organic solvent is used, a hydrophilic solvent described in International Publication No. 2004/069915 may be used for example.

A using amount of the hydrophilic organic solvent, although depending on type, particle size, and moisture content of the water absorbing resin particles, is preferably not more than 10 parts by mass relative to 100 parts by mass of the solid content of the water absorbing resin particles, and is more preferably in a range of not less than 0 parts by mass but not more than 5 parts by mass.

Moreover, inorganic acids, organic acids, polyamino acids and the like described in European Patent No. 0668080 may exist as the third material. These mixing auxiliary agents may work as the surface cross-linking agent, however is preferably one which does not decrease water absorbing ability of the water absorbing resin particles that are obtained after the surface cross-linking. The water absorbing resin particles used in the present invention is preferably cross-linked by (i) mixing the water absorbing resin particles with a surface cross-linking agent, which surface cross-linking agent does not contain a hydrophilic organic solvent having a boiling point of not more than 100° C., and (ii) heating this mixture. If the water absorbing resin particles contain the hydrophilic organic solvent having a boiling point of not more than 100° C., physical properties such as an SFC may not be sufficiently attained, due to a condition change of the surface cross-linking agent on the surface of the water absorbing resin particles caused by vaporization of the hydrophilic organic solvent.

In order to evenly mix the water absorbing resin particles and the surface cross-linking agent, it is preferable to have a water-soluble inorganic salt (more preferably persulfate) coexist with the water absorbing resin particles and the surface cross-linking agent, when the water absorbing resin particles and the surface cross-linking agent are mixed together. Although dependent on the type, particle size and the like of the water absorbing resin particles, a using amount of the water-soluble inorganic salt is preferably in a range of not less than 0.01 parts by mass but not more than 1 parts by mass relative to 100 parts by mass of the solid content of the water absorbing resin particles, and is more preferably in a range of not less than 0.05 parts by mass but not more than 0.5 parts by mass. Namely, the water absorbing resin particles are preferably cross-linked by (i) mixing the water absorbing resin particles with an organic surface cross-linking agent containing a water-soluble inorganic salt, preferably persulfate, and/or a water-soluble inorganic surface cross-linking agent in an amount not less than 0.01 mass % but not more than 1.0 mass % based on the water absorbing resin particles, and (ii) heating this mixture.

A mixing method for mixing the water absorbing resin particles and the surface cross-linking agent is not particularly limited. Examples of the methods that are possibly used encompass: a mixing method in which a surface cross-linking agent that is dissolved in water and/or a hydrophilic organic solvent if necessary is mixed with water absorbing resin particles which are soaked in the hydrophilic organic solvent; and a mixing method in which a surface cross-linking agent that is dissolved in water and/or a hydrophilic organic solvent is sprayed or dropped directly to the water absorbing resin particles.

After the water absorbing resin particles and the surface cross-linking agent are mixed, it is usually preferable to heat the mixture so as to carry out a cross-linking reaction. A heating temperature, although dependent on the surface cross-linking agent which is to be used, is preferably in a range of not less than 40° C. but not more than 250° C., is more preferably in a range of not less than 100° C. but not more than 240° C., and is further preferably not less than 150° C. but not more than 230° C. If the heating temperature is less than 40° C., absorbing properties such as the AAP and the SFC may not be sufficiently improved. The heating temperature exceeding 250° C. causes the water absorbing resin particles to deteriorate, which may cause various physical properties to decrease. Therefore, care is required in the heating temperature. Heating is preferably carried out for not less than 1 minute to not more than 2 hours, and more preferably for not less than 5 minutes to not more than 1 hour.

The water absorbing resin particles used in the present invention preferably have a mass median particle size in a range of not less than 100 μm but not more than 600 μm, more preferably in a range of not less than 200 μm but not more than 500 μm, and is most preferred to be in a range of not less than 300 μm but not more than 400 μm. If the mass median particle size of the water absorbing resin particles are not in the range of not less than 100 μm to not more than 600 μm, fluid permeability/diffusibility may significantly decrease, or absorbing speed may remarkably slow down. Use of such water absorbing resin particles, for example in disposable diapers, may cause leaking of fluid or the like.

The water absorbing resin particles used in the present invention preferably includes at least 50 mass % of water absorbing resin particles having a size in a range of not less than 175 μm to not more than 710 μm, and more preferably includes at least 80 mass % of the water absorbing resin particles of that size.

In addition, an amount of particles having a size which can pass through a sieve with openings of 150 μm thus included in the water absorbing resin particles used in the present invention is preferably not more than 5 mass %, more preferably not more than 3 mass %, and further preferably not more than 1 mass %, relative to the entire mass of the water absorbing resin particles. Use of the water absorbing resin particles including, relative to the entire mass of the water absorbing resin particles for the water absorbing agent, not more than 5 mass % of particles having the size which can pass through the sieve with openings of 150 μm, allows suppression of an amount of dust produced by the water absorbing resin thus obtained. Therefore, it is possible to prevent a safety and sanitation problem caused by dispersion of fine particles contained in the water absorbing resin particles at the time of producing the water absorbing agent. Moreover, it is possible to prevent decrease in physical property of the water absorbing agent thus obtained. If the amount exceeds 5 mass %, the dust is readily generated at the time of producing the water absorbing agent. As a result, the safety and sanitation problem may occur, or the physical property of the water absorbing agent may decrease.

Furthermore, as the water absorbing resin particles, fine water absorbing resin particles having a mass median particle size of not more than 300 μm (hereinafter suitably referred to as "fine powder") that are agglomerated, dried, adjusted in particle size and surface cross-linked may be used. Water absorbing resin particles which are obtained by partially mixing agglomerated products of the fine powder with water absorbing resin particles i.e., primary particles obtained by pulverization and having an irregularly-pulverized shape may also be used as the water absorbing resin particles. By thus partially mixing the agglomerated product of the fine powder with the water absorbing resin particles, a water absorbing agent having further excellent absorbing properties such as water absorbing speed, and fixed height absorption (FHA) as described in U.S. patent publication No. 2005/0003191A1, is obtainable. An amount mixed of the agglomerated product of the fine powder contained in the water absorbing resin particles is preferably at least 5 mass %, more preferably not less than 10 mass %, further preferably not less than 15 mass %, and most preferred to be not less than 20 mass %. Note that particle size of the fine powder is indicated by the mesh size of the sieve which is used for classifying the fine powder.

Known techniques for recycling the fine powder are adaptable, as a method for producing the agglomerated product of the fine powder. For example, the following methods are usable: a method in which warm water and the fine powder is mixed and dried (U.S. Pat. No. 6,228,930); a method in which the fine powder and a monomer aqueous solution is mixed and polymerized (U.S. Pat. No. 5,264,495); a method in which water is added to the fine powder so as to agglomerate by applying a specific plane pressure (European patent No. 844270); a method in which fine powder is sufficiently swollen so as to form an amorphous gel, then drying and crushing the amorphous gel (U.S. Pat. No. 4,950,692); and a method in which the fine powder and a polymerized gel is mixed (U.S. Pat. No. 5,478,879).

In particular, it is preferable to use the method in which the fine powder is mixed with warm water and is dried, as the production method of the agglomerated fine powder. Water absorbing resin particles agglomerated in this method has a porous structure (a same structure as a porous structure described in Japanese Unexamined Public Publication, Tokukai, No. 2004-261797), and therefore is preferable. It is preferable for the water absorbing resin particles used in the present invention to include particles having the porous structure by at least 5 mass %, more preferably not less than 10 mass %, further preferably not less than 15 mass %, and particularly preferably not less than 20 mass %. By thus having the water absorbing resin particles contain the agglomerated fine powder having the porous structure, the water absorbing resin particles and a water absorbing agent thus containing the water absorbing resin particles excel in the fixed height absorption (FHA).

A CRC of the water absorbing resin particles to be used in the present invention is preferably not less than 5 (g/g), more preferably not less than 15 (g/g), and further preferably not less than 25 (g/g). An upper limit of the CRC is not particularly limited, however is preferably not more than 60 (g/g), more preferably not more than 50 (g/g), and further preferably not more than 40 (g/g). The CRC less than 5 (g/g) causes an absorbing amount to be insufficient in order to be used as a water absorbing agent. Therefore, appropriate use in sanitary materials such as a disposable diaper and the like is not possible. If the CRC is more than 50 (g/g), attainment of a water absorbing agent having excellent fluid retaining speed in the absorbent core may be difficult, when the water absorbing resin particles are used in the water absorbing agent.

An AAP of the water absorbing resin particles to be used in the present invention is not less than 8 (g/g), preferably not less than 16 (g/g), more preferably not less than 20 (g/g), and further preferably not less than 21 (g/g). An upper limit of the AAP is not particularly limited, however is preferably not more than 30 (g/g). If the AAP is less than 8 (g/g), a water absorbing agent having few so-called rewet, which rewet occurs when the water absorbing agent is pressured, may not be attained.

The SFC of the water absorbing resin particles to be used in the present invention is preferably not less than 10 ($10^{-7} \cdot cm^3 \cdot s \cdot g^{-1}$), more preferably not less than 30 ($10^{-7} \cdot cm^3 \cdot s \cdot g^{-1}$), further preferably not less than 50 ($10^{-7} \cdot cm^3 \cdot s \cdot g^{-1}$), and particularly preferably not less than 100 ($10^{-7} \cdot cm^3 \cdot s \cdot g^{-1}$). The SFC less than 10 ($10^{-7} \cdot cm^3 \cdot s \cdot g^{-1}$) disables improvement in fluid permeability, thereby in a case where the water absorbing resin particles are used in the water absorbing agent, a water absorbing agent which excels in fluid retaining speed in the absorbent core may not be attained. An upper limit of the SFC is not particularly limited, however is preferably not more than 3000 ($10^{-7} \cdot cm^3 \cdot s \cdot g^{-1}$), and is more preferably not more than 2000 ($10^{-7} \cdot cm^3 \cdot s \cdot g^{-1}$). If the SFC is more than 3000 ($10^{-7} \cdot cm^3 \cdot s \cdot g^{-1}$), liquid leakage from the absorbent core may occur when the water absorbing resin particles are used in a water absorbing agent.

It is preferable for the water absorbing resin particles according to the present embodiment to have water soluble content of not more than 35 mass %, more preferably not more than 25 mass %, and further preferably not more than 15 mass %. If the water soluble content exceeds 35 mass %, the water absorbing resin particles weaken in gel strength, and become poor in liquid permeability. Moreover, when the water absorbing resin particles are used in the absorbing material, it may be difficult to obtain a water absorbing agent which can be applied to an absorbing material as a water absorbing agent from which an amount of liquid squeezed out (so-called re-wet) is little when a pressure is applied to the absorbing material.

(2) Organic Acid Having Carbon Number of 10 or More and not More than 30 in its Molecule The water absorbing agent of the present invention contains: organic acid whose carbon number is 10 or more and not more than 30 in its molecule and/or salt of the organic acid; and water-soluble polyvalent cation, on the surface of each of the water absorbent resin particles. The surface of each of the water-absorbent resin particles herein refers to: a portion of each of the water-absorbent resin particles which portion is exposed to the air; and/or a portion (shallow surface) to the above portion which portion (shallow surface) has a thickness of a tenth of the particle size (major axis). The major axis refers to the longest distance obtainable between two random points on the surface (portion exposed to the air) of each of the particles.

The presence of organic acid whose carbon number is 10 or more and not more than 30 in its molecule and/or salt of the organic acid and water-soluble polyvalent cation on the surface of each of the water absorbent resin particles allows improving the SFC of the water absorbing agent without causing a decrease in its CRC. In other words, this results in improvement in the liquid permeability of the water absorbing agent. The liquid permeability is improved as long as organic acid whose carbon number is 10 or more and not more than 30 in its molecule and/or salt of the organic acid and water-soluble polyvalent cation are contained in a portion of each of the water-absorbent resin particles which portion is exposed to the air and/or a portion adjacent to the above portion which portion has a thickness of a tenth of the particle size (major axis). However, when organic acid whose carbon number is 10 or more and not more than 30 in its molecule and/or salt of the organic acid and water-soluble polyvalent cation are contained in the portion of each of the water-absorbent resin particles which portion is exposed to the air, the physical properties of the water absorbing agent are further improved.

The organic acid is not particularly limited to a specific one. Examples of the organic acid include organic carboxylic acid, organic sulfonic acid, organic sulfinic acid, organic phosphinic acid, organic phosphonic acid, organic phosphoric acid, alkylsulfuric acid, amino acid, and salt (inorganic acid salt, organic acid salt) of the above. Among others, the organic acid for use in the present invention may preferably be a compound containing a carboxyl group in light of reactivity with polyvalent cation. Thus, the organic acid is more preferably organic carboxylic acid.

In addition, the organic acid may be a fatty acid, a petroleum acid, or a polymer acid. Among the above, the organic acid for use in the present invention may preferably be a fatty acid in light of safety, mixing property, and performance.

The organic acid is not particularly limited, provided that the number of carbon atoms in its molecule is 10 or more and not more than 30. However, the lower limit of the number of carbon atoms in the molecule is preferably 12 or more, and more preferably 14 or more. Further, the upper limit of the number is preferably 30 or fewer, and more preferably 24 or fewer. Since the number of carbon atoms in the molecule is 10 or more, the liquid permeability of the water absorbing agent is improved in a more effective, and therefore, favorable manner. The number of carbon atoms in the molecule is preferably 30 or fewer because, in that case, the mixing property and the use facility of the water absorbing agent are good, and also the SFC of the water absorbing agent is improved more effectively.

Hydrophobic groups in the organic acid and/or salt of the organic acid, which groups are present among the water absorbent resin particles, apparently collect and become stable, instead of dissolving in water, among the water absorbent resin particles due to hydrophobic interaction. This allows the water absorbent resin particles to be a stable distance apart from one another, and thereby apparently improving the liquid permeability of the water absorbing agent.

The organic carboxylic acid may be linear, branched, or cyclic. The organic carboxylic acid may further be saturated or unsaturated. More specifically, examples of the organic carboxylic acid include: unsaturated fatty acids such as hexadecenoic acid (palmitoyl acid), cis-9-octadecenoic acid (olein acid), 11-octadecenoic acid (vaccenic acid) cis,cis-9, 12-octadecadienoic acid (linoleic acid), octadecatrienoic acid (linolenic acid), beef fatty acid, and hydrogenated castor oil fatty acid; saturated acids such as decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid (tuberculostearic acid), icosanic acid (arachic acid), docosanoic acid (behenic acid), tetradocosanoic acid (lignoceric acid), hexadocosanoic acid (cerotic acid), and octadocosanoic acid (montanic acid, melissic acid); petroleum acids such as benzoic acid, myristicinic acid, naphthenic acid, naphthoic acid, and naphthoxyacetic acid; and polymer acids such as polysulphonic acid.

The organic acid used in the present invention is preferably a fatty acid whole molecule has a hydrocarbon chain of 9 or more carbon atoms therein. This provides a long hydrocarbon chain between the water absorbent resin particles. Thereby, it is expected that the hydrophobic groups of the fatty acids existing between the water absorbent resin particles remain undissolved in water but cause stable aggregation between the water absorbent resin particles due to their hydrophobic interaction. This provides a stable gap between the water absorbent resin particles, thereby attaining liquid permeability. The hydrocarbon chain can be any hydrocarbon chain having 9 or more carbon atoms. It is more preferable that the hydrocarbon chain has 11 or more carbon atoms. It is further preferable that the hydrocarbon chain has 13 or more carbon atoms. It is more preferable that the upper limit is the number of carbon atoms in the hydrocarbon chain is 29 or less, in view of mixing property, handleability, and SFC improvement. In case where two or more types of organic acids are used, the number of the carbon atoms is an average in numbers of the carbon atoms of the organic acids. The organic acid used in the present invention may be another organic acid having in its molecule a hydrocarbon chain having 9 or more carbon atoms.

The hydrocarbon chain may be saturated or unsaturated. That is, the hydrocarbon chain may have one or more double bonds therein, and/or one or more triple bonds therein.

Among others, the organic acid for use in the present invention is more preferably a fatty acid containing in its molecule a linear alkyl chain whose carbon number is 9 or more. This allows a long alkyl chain to be present among the water absorbent resin particles. As a result, hydrophobic groups of the fatty acid, which are present among the water absorbent resin particles, remain undissolved in water and causes stable aggregation between the water absorbent resin particles due to hydrophobic interaction. This provides a stable gap between the water absorbent resin particles, thereby attaining liquid permeability. The alkyl chain is only required to be an alkyl chain whose carbon number is 9 or more. However, the alkyl chain is preferably an alkyl chain whose carbon number is 11 or more, and more preferably an alkyl chain whose carbon number is 13 or more. There is no particular upper limit to the number of carbon atoms in the alkyl chain. However, the number is preferably 29 or fewer in light of mixing property and use facility of the water absorbing agent and improvement in the SFC of the water absorbing agent. The fatty acid may be a saturated or unsaturated fatty acid, provided that the fatty acid contains a linear alkyl chain whose carbon number is 9 or more. In a case where two ore more organic acids are used, the number of the carbon atoms is an average in numbers of the carbon atoms of the organic acids. In addition, another organic acid containing in its molecule a linear alkyl chain whose carbon number is 9 or more may also be preferably used as an organic acid for use in the present invention. Examples of such another organic acid include alkylsulfuric acid, alkylbenzenesulfonic acid, alkylphosphonic acid, alkylphosphine acid, and alkylphosphoric acid.

One of the above organic acids may be individually used, or two or more of the above organic acids may be used in combination.

Salt of the organic acid for use in the present invention is not particularly limited, either. However, the salt is preferably made of organic acid and univalent cation. Specifically, examples of the salt include salt of alkali metals such as sodium, potassium, and lithium, ammonium salt, amine salt, and triethanolamine salt. The salt is preferably made of the organic acid and univalent cation because such salt is readily reactive with polyvalent cation (described below) and excels in performance.

The salt of the organic acid is not particularly limited, provided that the salt is formed by combination of the above organic acid and the above salt. In addition, one kind of the salt of the organic acid may be individually used, or two or more kinds of the salt of the organic acid may be used in combination.

Further, either the organic acid whose carbon number is 10 or more and not more than 30 in its molecule or salt of the organic acid may be individually present on the surface of each of the water absorbent resin particles. Alternatively, a mixture of the organic acid and the salt may be present thereon.

(3) Water-Soluble Polyvalent Cation

The water absorbing agent according to the present invention includes water absorbent resin particles, wherein an organic acid and/or salt thereof and a water-soluble polyvalent cation exist on a surface of each of water absorbent resin particles. The polyvalent cation used in the present invention is not particularly limited provided that it is a water-soluble polyvalent cation. As being water-soluble, the polyvalent cation is more likely to interact with the organic acid (salt) and the water absorbent resin particles. Thus, it is possible to obtain a water absorbing agent which is excellent in a balance between a centrifugal retention capacity (CRC) and a saline flow conductivity (SFC).

"Water-soluble" used herein means a condition under which 1 g or more of the polyvalent cation dissolves in 100 g of water whose temperature is 25° C. As such, the polyvalent cation used in the present invention is suitable if 1 g or more, more preferably 10 g or more, and most preferably 20 g or more, of the polyvalent cation dissolves in 100 g of water whose temperature is 25° C.

The water-soluble polyvalent cation used in the present invention is not particularly limited provided that it is bivalent or more cation. As such, for example, water-soluble polyvalent metal salt, a water-soluble cationic polymer compound, or the like can be suitably used.

As water-soluble polyvalent metal salt used in the present invention, the following can be suitably used: for example, aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, zirconium nitrate, zirconium ammonium carbonate, zirconium potassium carbonate, zirconium sodium carbonate, and the like. It is particularly preferable to use an aluminum compound as the water-soluble polyvalent metal salt used in the present invention. More suitably, the followings can also be used as the water-soluble polyvalent metal salt used in the present invention: aluminum chloride, poly aluminum chloride, aluminum sulfate, aluminum nitrate, bis aluminum potassium sulfate, bis aluminum sodium sulfate, potassium alum, ammonium alum, sodium alum, sodium aluminate, and the like.

In terms of solubility in aqueous liquid to be absorbed, it is more preferable that the water-soluble polyvalent metal salt is water-soluble polyvalent metal salt having a crystal water.

The water-soluble polyvalent metal salt may be used either independently or in a combination with two or more kinds.

It is particularly preferable that the water-soluble polyvalent metal salt used in the present invention is aluminum sulfate, aluminum sulfate octadecahydrate, or aluminum sulfate hydrate (tetradecahydrate to octadecahydrate).

In the present invention, it is preferable that the water-soluble polyvalent metal salt is mixed with the water-absorbent resin, as aqueous liquid. In such case, it is preferable in view of the mixing property and the SFC improvement effect that concentration of the water-soluble polyvalent metal salt ranges from 30 mass % to a saturation concentration. When the water-soluble polyvalent metal salt has the concentration of 30 mass % or more, the water-soluble polyvalent metal salt is prevented from permeating the water absorbent resin particle, thereby allowing the even mixture and the increase in the SFC improvement effect. Besides, when the water-soluble polyvalent metal salt has the concentration of the saturation concentration or less, the dust powder caused by the precipitation of the salt is prevented from being developed.

The followings can be used as the water-soluble cationic polymer compound used in the present invention: for example, polyethylenimine, polyamine, modified polyamideamine denaturalized by graft of ethylenimine, protonated polyamideamine, condensates of polyamideamine and epichlorohydrin, condensates of amines and epichlorohydrin, poly(vinylbenzyldialkylammonium), poly(diallylalkylammonium), poly(2-hydroxy-3-methacryloyloxyproplydialkylamine), polyetheramine, polyvinylamine, modified polyvinylamine, partial hydrolysate of poly(N-vinylformamide), partial hydrolysate of poly(N-vinylalkylamide), partial hydrolysate of a copolymer of (N-vinylformamide)-(N-vinylalkylamide), polyalkylamine, polyvinylimidazole, polyvinylpyridine, polyvinylimidazoline, polyvinyltetrahydropyridine, polydialkylaminoalkylvinylether, polydialkylaminoalkyl(meth)acrylate, polyallylamine, polyamizine, a cationized product such as starch or cellulose, or the like; salt thereof; or a reactant with electrophilic agent thereof or the like.

These water-soluble cationic polymer compounds may be used either independently or in a combination with two or more kinds.

The water-soluble cationic polymer compound used in the present invention has a weight average molecular weight preferably in a range of 2000 or more, more preferably in a range of 5000 or more, and most preferably in a rage of 10000 or more. If the weight average molecular weight is less than 2000, an expected effect may not be obtained. An upper limit of the weight average molecular weight of the cationic polymer compound is not particularly limited. However, the weight average molecular weight of the cationic polymer compound is preferably in a range of 1,000,000 or less, and more preferably in a range of 500,000 or less. This is because, when the weight average molecular weight of the cationic polymer compound is 1,000,000 or less, viscosity becomes lowered, providing a better handling and mixing property. The weight average molecular weight can be measured by conventional method such as GPC, viscosity measurement, static light scattering or the like.

The water absorbing agent of the present invention should include water absorbing resin particles, an organic acid and/or salt thereof having carbon number of 10 or more and not more than 30 in its molecule, and water-soluble polyvalent cation. It is more preferable that the water absorbing agent further includes water-insoluble inorganic particles as an additive. It is still more preferable that the water absorbing agent of the present invention further includes the water-insoluble inorganic particles on the surface of the water absorbing resin particles. The surface of the water absorbing resin particles has been already explained above. Whether the water-unsoluble inorganic particles exist on the surface of the water absorbing resin particles or not can be confirmed with a scanning electron microscope (SEM) etc.

When the water absorbing agent includes the water-insoluble inorganic particles, it is possible to improve liquid-permeability of the water absorbing agent and to further improve handleability of the water absorbing agent when absorbing water.

Specific examples of the water-insoluble inorganic particles include minerals such as talc, clay, kaolin, fuller's earth, bentonite, activated clay, barite, natural asphaltum, strontium ore, ilmenite, and pearlite; metal oxides such as silicon dioxide and titanium oxide; silicic acid (salt) such as natural zeolite and synthetic zeolite; water-insoluble polyvalent metal salts such as calcium sulfate and aluminum oxide; hydrophilic amorphous silica (e.g., Aerosil 200 produced by NIPPON AEROSIL CO., LTD., dry method: ReolosilQS-20 produced by TOKUYAMA corp., precipitation method: and Sipernat 22S and Sipernat 2200 produced by DEGUSAA); mixed hydrate oxides including zinc and silicon or zinc and aluminum (shown in International Publication WO2005/010102); and mixed oxides such as silicon oxide-aluminum oxide-magnesium oxide complex (e.g., Attagel #50 produced by ENGELHARD), silicon oxide-aluminum oxide complex and silicon oxide-magnesium oxide complex. Further, the water-insoluble inorganic particles shown in U.S. Pat. No. 5,164,459, EP Patent No. 761241, etc. may be used. Among them, silicon dioxide and silicic acid (salt) is preferable, and silicon dioxide and silicic acid (salt) that are fine particles whose average particle size measured by a coulter counter method ranges from 0.001 to 200 µm is more preferable.

It is preferable that the water-insoluble inorganic particles have primary particles whose average particle size ranges from 5 to 50 nm and 90 mass % or more of the water-insoluble inorganic particles are agglomeration of the primary particles. Further, it is preferable that mass median particle size of agglomeration of the primary particles is 20 µm or less.

Further, it is preferable that specific surface area of the water-insoluble inorganic particles that is measured by a BET method ranges from 30 to 330 $m^2/g$.

In particular, it is still more preferable that the water absorbing agent of the present invention includes silicon dioxide as the water-insoluble inorganic particles. It is still more preferable that the silicon dioxide is amorphous fumed silica (which may be hereinafter referred to as amorphous silica) produced by dry method. Silicon dioxide called quartz is not preferable in the present invention since quartz may raise a health problem.

(4) Water Absorbing Agent

The water absorbing agent of the present invention is a water absorbing agent including water absorbent resin particles, organic acid and/or salt thereof having carbon number of 10 or more and not more than 30 in its molecule and water-soluble polyvalent cation. More specifically, the water absorbing agent of the present invention is a water absorbing agent including water absorbent resin particles, wherein organic acid and/or salt thereof having carbon number of 10 or more and not more than 30 in its molecule and water-soluble polyvalent cation exist on a surface of each of the water absorbent resin particles. It should be noted that because the organic acid and/or salt thereof having carbon number of 10 or more and not more than 30 in its molecule and the water-soluble polyvalent cation were explained in (2) and (3), and the water absorbent resin particles were explained in (1), they are not explained repeatedly.

More preferably, the water absorbing agent of the present invention is obtained by polymerizing a water-soluble unsaturated monomer, has an internally crosslinked structure, and includes surface crosslinked water absorbent resin particles and the organic acid and/or salt thereof having carbon number of 10 or more and not more than 30 in its molecule and the water-soluble polyvalent cation, and it is preferable that the organic acid whose carbon number is 10 or more and not more than 30 in its molecule and/or salt thereof and the water-soluble polyvalent cation exist between the water absorbing resin particles and/or on a surface of each of the water absorbent resin particles at the time of water absorption. This makes it possible to increase the CRC and to obtain an amazing liquid permeability improvement which cannot be obtained in conventional arts. One of the reasons is that hydrophobic groups included in the organic acid and/or salt thereof causes stable aggregation between water absorbent resin particles due to a molecular bonding by hydrophobic interaction between the hydrophobic groups, on which water absorbent resin particles the organic acid and/or salt thereof exist. Therefore, a stable space is formed between the water absorbent resin particles, and liquid permeability is improved. Further, although the reason is not clear, it is impossible to obtain the liquid permeability-improvement when only the organic acid and/or salt thereof or the water-soluble polyvalent cation is used. Therefore, when the organic acid and/or salt thereof and the water-soluble polyvalent cation synergistically interact with each other, it is possible to obtain the remarkably excellent liquid permeability-improving effect.

Further, each of the water absorbent resin particles on which surface the organic acid and/or salt thereof having carbon number of 10 or more and not more than 30 in its molecule and the water-soluble polyvalent cation exist has a mass median particle size of preferably 100 µm or more and 600 µm or less, more preferably 200 µm or more and 500 µm or less, still more preferably 300 µm or more and 400 µm or less. When the mass median particle size exceeds this range, there is a case where the liquid permeability declines and the speed of water absorption into the water absorbing agent drops. That is, an absorption rate deteriorates. This may result in problems such as a liquid leakage when used in a disposable diaper or the like.

The water absorbing agent including the water absorbent resin particles of 175 µm or more and 710 µm or less is preferably 50 mass % or more, and preferably 80 mass % or more, the organic acid and/or salt thereof having carbon number of 10 or more and not more than 30 in its molecule and the water-soluble polyvalent cation existing on a surface of each of the water absorbent resin particles.

Further, in the water absorbing agent, among the water absorbent resin particles on which surface the modified cationic polymer compound exists, particles which can pass through a sieve having a mesh size of 150 µm is preferably 5 mass % or less, more preferably 3 mass % or less, and most preferably 1 mass % or less. When the water absorbent resin particles which can pass through a sieve having a mesh size of 150 µm is more than 5 mass %, problems of safety and hygiene are caused due to scattering of the particles at the time of manufacturing a water absorbing agent. Further, there is a case where properties of the obtained water absorbing agent deteriorate.

Further, in the water absorbing agent, in each of the water absorbent resin particles on which surface the organic acid and/or salt thereof having carbon number of 10 or more and not more than 30 in its molecule and the water-soluble polyvalent cation exist, a logarithmic standard deviation ($\sigma\zeta$) of a particle size distribution preferably is 0.20 or more and 0.50 or less, more preferably 0.30 or more and 0.40 or less. When the mass median particle size exceeds this range, there is a case where the liquid permeability declines and the speed of water absorption into the water absorbing agent drops.

In the water absorbing agent, its CRC is preferably 5 (g/g) or more, more preferably 15 (g/g) or more, still more preferably 25 (g/g) or more. An upper limit of the CRC is not limited in particular, but is preferably 60 (g/g) or less, more preferably 50 (g/g) or less, still more preferably 40 (g/g) or less. When the CRC is less than 5 (g/g), an amount of water absorption is too small. Therefore, the water absorbing agent having the CRC of less than 5 (g/g) cannot be suitably used in a sanitary material such as a disposable diaper. Further, when the centrifuge retention capacity (CRC) is more than 60 (g/g), it may be impossible to obtain a water absorbing agent excellent in speed of the water absorption into an absorbing material when used in the absorbing material.

In the water absorbing agent of the present invention, the saline flow conductivity (SFC) is preferably 30 ($10^{-7} \cdot cm^3 \cdot s \cdot g^{-1}$) or more, more preferably 50 ($10^{-7} \cdot cm^3 \cdot s \cdot g^{-1}$) or more, further preferably 100 ($10^{-7} \cdot cm^3 \cdot s \cdot g^{-1}$), further more preferably 150 ($10^{-7} \cdot cm^3 \cdot s \cdot g^{-1}$) or more, particularly preferably 170 ($10^{-7} \cdot cm^3 \cdot s \cdot g^{-1}$) or more, most preferably 200 ($10^{-7} \cdot cm^3 \cdot s \cdot g^{-1}$) or more. When the SFC is less than 30 ($10^{-7} \cdot cm^3 \cdot s \cdot g^{-1}$), it may be impossible to obtain a water absorbing agent excellent in speed of the water absorption into an absorbing material when used in the absorbing material. An upper limit of the SFC is not limited in particular, but is preferably 3000 ($10^{-7} \cdot cm^3 \cdot s \cdot g^{-1}$) or less. When the SFC exceeds this upper limit, the problems mentioned in the section of the water absorbent resin particles may be caused.

In the water absorbing agent of the present invention, an absorbency against pressure (AAP) is preferably 8 (g/g) or more, more preferably 16 (g/g) or more, still more preferably 20 (g/g) or more where the pressure is 4.83 kPa. An upper limit of the AAP is not limited in particular, but is preferably 30 (g/g) or less. When the absorbency against pressure (AAP) is less than 8 (g/g) where the pressure is 4.83 kPa, it may be impossible to obtain a water absorbing agent which can be applied to an absorbing material as a water absorbing agent from which an amount of liquid squeezed out (so-called re-wet) is little when a pressure is applied to the absorbing material.

The water absorbing agent has an water-soluble content of preferably 35 mass % or less, more preferably 25 mass % or less, still more preferably 15 mass % or less. In case where the water-soluble content exceeds 35 mass %, its gel strength may be low and its liquid permeability may be low. Further, in case where the water absorbing agent is used in a disposable diaper for an extended period of time, the CRC, the AAP and the like may drop as time elapses.

Further, the water absorbing agent of the present invention is preferably has the hydrophilic property. In order that the water absorbing agent may have the hydrophilic property, it is possible to appropriately use conventionally known methods such as a method in which a water absorbent resin containing, at least on its surface, quadrivalent polyol or polyol of a greater valency is used (WO2005/044915), a method in which inorganic fine particles are added on a water absorbent resin and UV light is irradiated on the water absorbent resin (Japanese Unexamined Patent Publication No. 2006-233008), a method in which a water absorbing agent composition including water-insoluble inorganic fine particles and fulfilling specific conditions is used (Japanese Patent Application No. 2007-504791), a method in which a water absorbent resin including a water-soluble polyvalent metal salt and a urea derivative is used (U.S. Patent Application Publication No. 2005-0288182), and a method in which hydrophilic inorganic fine particles are added (Japanese Patent Application No. 2006-188668).

(5) Method for Producing a Water Absorbing Agent

The present invention encompasses a method for producing a water absorbing agent including water absorbent resin particles, organic acid and/or salt thereof having carbon number of 10 or more and not more than 30 in its molecule and water-soluble polyvalent cation. More specifically, The present invention encompasses a method for producing a water absorbing agent including water absorbent resin particles, wherein organic acid and/or salt thereof having carbon number of 10 or more and not more than 30 in its molecule and water-soluble polyvalent cation exist on a surface of each of the water absorbent resin particles. The method according to the present invention for producing the water absorbing agent only needs to include at least a mixing step of mixing the water absorbent resin particles, the organic acid and/or salt thereof having carbon number of 10 or more and not more than 30 in its molecule, and the water-soluble polyvalent cation with one another. Thus, it is possible to provide a water absorbing agent which is excellent in a balance between a CRC and an SFC.

In the present invention, the mixing step of mixing the water absorbent resin particles, the organic acid and/or salt thereof, and the water-soluble polyvalent cation with one another is not limited to any particular method, but may use any one of the following methods: (i) a method for mixing the water absorbent resin particles with (a) a solution or a dispersion solution each of which includes the organic acid and/or salt thereof and (b) a solution or a dispersion solution each of which includes the water-soluble polyvalent cation; (ii) a method for spraying, onto the water absorbent resin particles, (a) the solution or the dispersion solution each of which includes the organic acid and/or salt thereof and (b) the solution or the dispersion solution each of which includes the water-soluble polyvalent cation, and for mixing the resultant; and (iii) a method for directly adding the organic acid and/or salt thereof or the water-soluble polyvalent cation to the water absorbent resin particles, for adding, as needed, water, a solvent, a dispersion solvent, or the like thereto, and for mixing the resultant.

In the method according to the present invention for producing the water absorbing agent, the organic acid and/or salt thereof or the water-soluble polyvalent cation may be directly mixed with the water absorbent resin particles. However, it is more preferable that a solution or dispersion solution of the organic acid and/or salt thereof, or a solution or dispersion solution of the water-soluble polyvalent cation is mixed with the water absorbent resin particles. This is preferable because this allows even mixture.

It is further preferable to arrange the method according to the present invention for producing the water absorbing agent so that a solution, an emulsification solution, or a suspension solution of the organic acid and/or salt thereof is mixed with the water absorbent resin particles.

In a case where a solution of the organic acid and/or salt thereof is mixed with the water absorbent resin particles, a solvent to be used is not limited to any particular kind, but may preferably be, for example, water and an organic solvent such as an alcohol (e.g., ethanol, methanol, propylene glycol, and glycerin), hydrocarbon, or polyethylene glycol. Also, it is preferable that a concentration of the organic acid and/or salt thereof in the solution is at least 10 mass % but 90 mass % or less, more preferably at least 30 mass % but 80 mass % or less.

In a case where a suspension solution of the organic acid and/or salt thereof is mixed with the water absorbent resin particles, a dispersion solvent to be used is not limited to any particular kind, but may preferably be, for example, water and an organic solvent such as an alcohol. Particularly, it is more preferable to use water. Also, it is preferable that a concentration of the organic acid and/or salt thereof in the dispersion solution is at least 10 mass % but 90 mass % or less, more preferably at least 30 mass % but 80 mass % or less. Further, a dispersion agent such as water-soluble polymer, surfactant, or polyethylene glycol may be added thereto.

Besides the solution or the suspension solution, the organic acid and/or salt thereof may be in a form of an emulsification solution when mixed with the water absorbent resin particles. In the emulsification solution, the organic acid and/or salt is emulsified with emulsification agent in a dispersion solvent. In this case, a dispersion solvent to be used is not limited to any particular kind, but may preferable be, for example, water and an organic solvent such as an alcohol. The emulsification agent is not limited to any particular kind, but may be a nonionic surfactant, an amphoteric surfactant, an anionic surfactant, or the like. Also, it is preferable that a concentration of the organic acid and/or salt thereof in the emulsification solution is at least 10 mass % but 90 mass % or less, more preferably at least 30 mass % but 80 mass % or less.

It is further preferable to arrange the method according to the present invention for producing the water absorbing agent so that an aqueous solution of the water-soluble polyvalent cation is mixed with the water absorbent resin particles. Also, it is preferable that a concentration of the water-soluble polyvalent cation in the aqueous solution is at least 10 mass % but a value of a saturated concentration or less, more preferably at least 20 mass % but the value of the saturated concentration or less.

Also, it is not particularly limited in which order the organic acid and/or salt thereof and the water-soluble polyvalent cation are mixed with the water absorbent resin particles. However, it is preferable that the organic acid and/or salt thereof is mixed with the water absorbent resin particles (i) at a point where the water-soluble polyvalent cation is added or (ii) before the water-soluble polyvalent cation is added. Particularly, it is more preferable that the organic acid and/or salt thereof is mixed with the water absorbent resin particles before the water-soluble polyvalent cation is added. This attains a higher CRC and a more excellent liquid permeability improving effect.

Also, it is not particularly limited in which phase the foregoing mixing step is carried out. The mixing step may be carried out in any phase as far as the polymerization of the water absorbent resin has been done. It is preferable that the water absorbent resin particles used in the present invention are the ones which have been crosslinked in its shallow surface. Also, in a case where such water absorbent resin particles are used, it is further preferable that the mixing step is carried out during and/or after a surface cross-linking step for cross-linking, by using a surface cross-linking agent, the water absorbent resin particles in its shallow surface. In this case, the method according to the present invention for producing the water absorbing agent further includes a surface cross-linking step of cross-linking, by using the surface cross-linking agent, the surface of the water absorbent resin obtained by the polymerization.

The phase during and/or after the surface cross-linking step, in each of which phase the mixing step is carried out, may be: a phase at the point when the water absorbent resin is mixed with the surface cross-linking agent; a phase during a mixture of the water absorbent resin and the surface cross-linking agent is being heated; a phase immediately after the heating of the mixture of the water absorbent resin and the surface cross-linking agent; a phase after cooling of the water absorbent resin particles obtained by heating the mixture of the water absorbent resin and the surface cross-linking agent; or a plurality of phases described above.

Particularly, in view of a purpose for attaining a high CRC and a more excellent liquid permeability improvement, it is preferable to carry out the mixing step after the surface cross-linking step. For example, it is more preferable to carry out the mixing step immediately after the heating of the mixture of the water absorbent resin and the surface cross-linking agent or after cooling of the water absorbent resin particles obtained by heating the mixture of the water absorbent resin and the surface cross-linking agent. Further, it is particularly preferable to carry out the mixing step after the cooling of the water absorbent resin particles obtained by heating the mixture of the water absorbent resin and the surface cross-linking agent.

Further, in the mixing step, at a point when the water absorbent resin particles are mixed with the organic acid and/or salt thereof and the water-soluble polyvalent cation or after the water absorbent resin particles are mixed with the organic acid and/or salt thereof and the water-soluble polyvalent cation, it is preferable to maintain the mixture thus obtained at a temperature of at least 30° C. but less than 150° C., more preferably at a temperature of at least 40° C. but less than 100° C., for 1 minute to 240 minutes, more preferably for 10 minutes to 120 minutes.

Also, in the mixing step, a concrete method for mixing the water absorbent resin particles, the organic acid whose carbon number is 10 or more and not more than 30 in its molecule and/or salt thereof, and the water-soluble polyvalent cation with one another is not particularly limited, but may use any known stirring device. Examples of the stirring device preferably used encompass: a puddle blender; a ribbon mixer, a rotary blender; a jar tumbler; a Plauger mixer; a mortar mixer; a cylindrical mixer; a screw type mixer; a screw type extruder; a turbulizer; a Nauter type mixer; a V-type mixer; a double-arm kneader; a fluidization mixer; an air mixer; a rotating disc mixer; a roll mixer; a tumbling mixer; and a Loedige mixer. Further, the stirring device may include: a heating device for heating a mixture of the water absorbent resin particles, the organic acid whose carbon number is 10 or more and not more than 30 in its molecule and/or salt thereof, and the water-soluble polyvalent cation; or a cooling device for cooling the mixture heated by the heating device. Time any one of the stirring devices takes to carry out a stirring process is not particularly limited, but may preferably be 60 minutes or less, more preferably 30 minutes or less.

In the method for producing the water absorbing agent, it is preferable to mix the organic acid whose carbon number is 10 or more and not more than 30 in its molecule and/or salt thereof, the water-soluble polyvalent cation, and the water absorbent resin particles with one another, after the water absorbent resin particles are subjected to mechanical damage so as to have an irregularly-pulverized shape. The water absorbent resin particles having the irregularly-pulverized shape can efficiently contain, at least either on its surface or in the shallow surface, the organic acid whose carbon number is 10 or more and not more than 30 in its molecule and/or salt thereof and the water-soluble polyvalent cation. Thus, it is possible to improve properties of the water absorbing agent thus obtained.

The "mechanical damage" herein means that the water absorbent resin particles are collided with a piece of glass or metal so that the water absorbent resin particles are subjected to a physical shock.

A method for giving mechanical damage to the water absorbent resin particles is not particularly limited, but only needs to be capable of giving a shock to the water absorbent resin particles. Examples of this method encompass a method (paint shaker test) for shaking a glass container containing water absorbent resin particles and glass beads so that the water absorbent resin particles are subjected to mechanical damage. Another method for giving mechanical damage to the water absorbent resin particles may be: a method (ball mill) for rotating a cylindrical container containing water absorbent resin particles and a ball or the like; a method for stirring water absorbent resin particles in a stirring device having a stirring wing; a method for passing water absorbent resin particles through a paddle dryer (a heating device or a cooling device each of which has a paddle wing); a method for crushing water absorbent resin particles by means of a crushing device; a method for conveying water absorbent resin particles by air stream; or a method for causing a collision or friction between one particle of a water absorbing resin particle and another particle of the water absorbing resin particle.

The above-mentioned paint shaker test (PS) is a method for (i) putting 10 g of glass beads having a 6 mm diameter and 30 g of the water absorbent resin or 30 g of the water absorbing agent into a glass container having a 6 cm diameter and a 11 cm height, (ii) attaching the glass container to Paint Shaker (Toyo Seiki Seisaku-sho, Ltd., product No. 488), and (iii) shaking the glass container at 800 cycle/min (CPM). The detail of the device is disclosed in Japanese Unexamined Patent Application Publication, Tokukaihei, No. 9-235378.

Shaking time is in a range from 10 minutes to 30 minutes. After the shaking, the glass beads are removed by using a JIS standard sieve (mesh opening: 2 mm), so as to obtain water absorbent resin particles subjected to damage.

(6) Water Absorbing Material

In the present invention, the water absorbing material includes the water absorbing agent according to the present invention. A combination of the water absorbing material and an appropriate material can be used as, for example, a water absorbing core suitable as a water absorbing layer of the sanitary material. The following explains the water absorbing material.

The water absorbing material is a composition made of the water absorbing agent and other material, and formed in a desired shape. The water absorbing material is used in a sanitary material for a disposable diaper, a sanitary napkin, an incontinence pad, a medical pad, and the like, each of which absorbs blood, bodily fluid, urine, and the like. An example of the material used for the water absorbing material encompasses a cellulose fiber. A specific example of the cellulose fibers encompasses a wood pulp fiber such as a mechanical pulp made from wood, a chemical pulp, a semi-chemical pulp, and a dissolved pulp, an artificial cellulose fiber such as rayon and acetate, and the like. A preferable cellulose fiber is a wood pulp fiber. These cellulose fibers may partially contain a synthesized fiber such as a nylon and a polyester. When the water absorbing agent of the present invention is used as a part of the water absorbing material, weight of the water absorbing agent in the water absorbing material is preferably 20 mass % or more, more preferably 30 mass % or more, and most preferably 40 mass % or more. If the water absorbing agent of the present invention in the water absorbing material have weight of less than 20 mass %, there is a risk that a sufficient effect can not be obtained.

For obtaining the water-absorbing material by using the water absorbing agent and the cellulose fibers, for example, the following conventional methods may be adopted as appropriate: a method for obtaining the water absorbing material by dispersing the water absorbing agent on a paper sheet or mat made of the cellulose fibers, and if necessary, by sandwiching the water absorbing agent between the paper sheets or mats; a method for obtaining the water absorbing material by blending the cellulose fibers and the water absorbing agent uniformly; and the like methods. A more preferable method encompasses a method for obtaining the water-absorbing material by dry-mixing the water absorbing agent and the cellulose fibers to obtain a mixture of them, and then compressing the mixture. This method significantly prevents fall-out of the water absorbing agent from the cellulose fibers. It is preferable that the compression be carried out while heating the mixture. The heating is carried out, for example, at a temperature in a range of 50° C. to 200° C.

The water absorbing agent according to the present invention is excellent in solid state properties. Thus, when using the water absorbing agent in the water absorbing material, it is possible to obtain the highly excellent water absorbing material that quickly absorbs liquid and leaves less residual liquid in a surface layer of the water absorbing material.

These excellent water absorbing properties allow the water absorbing agent of the present invention to be used as a water absorbing retaining agent for various usages, for example: a water absorbing retaining agent for absorbing goods such as a disposable diaper, a sanitary napkin, an incontinence pad, a medical pad, and the like; a water retaining agent for agriculture/horticulture, such as a substitute for sphagnum moss, a soil conditioner, a water retaining agent, an agrichemical effect keeping agent, and the like; a water retaining agent for construction/civil engineering usages, such as a dew condensation preventing agent for an interior wall material, an additive for cement, and the like; a release controlling agent, a cold insulating agent, a disposable body warmer, a coagulant for polluted mod, a freshness preserving agent for a food, an ion exchanging column material, a dehydrating agent for sludge/oil, a desiccant agent, a humidity conditioning agent, and the like. Particularly, the water absorbing agent of the present invention is suitable for use in a sanitary material (such as a disposable diaper, a sanitary napkin, and the like) for absorbing excrement, urine, and/or blood.

In a case where the water absorbing material is used in the sanitary material for the disposable diaper, sanitary napkin, incontinence pad, medical pad, or the like, it is preferable that the water absorbing material is used in such an arrangement that includes (a) a liquid-permeable top sheet to be next to a body of a user, (b) a liquid-impermeable back sheet to be next to cloths of the user but far away from the body of the user, and (c) a water absorbing material provided between the top sheet and the back sheet. The water absorbing material may be multi-layered (two or more layers). Further, the water absorbing material may be used in combination with a pulp layer or the like.

EXAMPLES

Through the following Examples, the present invention is further described. However, the present invention is not limited to the following Examples. In the following examples, "part by weight" may be described, for convenience, as "part", and "litter" as "L". Further, "% by mass" may be described as "wt %".

Properties of a water absorbent resin, or a water absorbing agent were measured in the following measurement method. Without any special descriptions, the following measurement was conducted at room temperature (20 to 25° C.) and humidity of 50 RH %.

In a case of a water absorbing agent that has been used as a final product such as a sanitary material, the water absorbing agent absorbs moisture. In this case, the water absorbing agent may be appropriately separated from the final product and dried under low pressure and at low temperature (for example, dried under not more than 1 mmHg and at 60° C. for 12 hours), so that the resultant thus obtained may be measured. Further, each solid content of the water absorbing agents used in Examples and Comparative Examples was not less than 94 wt %. The following descriptions of measurement methods deal with measurements of the water absorbing agent as an example, but properties of water absorbent resin particles also can be measured in the same manner.

<Centrifuge Retention Capacity (CRS)>

The centrifuge retention capacity (CRC) represents an absorption capacity at which 0.90 wt % of saline is absorbed for 30 minutes without load. The CRC is also referred to as absorption capacity without load.

Then, 0.200 g of water absorbing agent was evenly contained in a bag (85 mm×60 mm) made of a nonwoven fabric (manufactured by Nangoku Pulp Kogyo Co., Ltd., Heatron Paper: model type is GSP-22) and was heat-sealed. Then, the bag was soaked in an excessively large amount (generally, about 500 ml) of 0.90 wt % saline (sodium chloride aqueous solution) at room temperature, and was withdrawn 30 minutes later. By use of a centrifugal separator (manufactured by KOKUSAN corporation, centrifugal machine: model type is H-122), the bag was drained for three minutes at centrifugal force (250G) described in edana ABSORBENCY II 441.1-99, and a weight W1 (g) of the bag was measured. Further, the same operation was performed without using the water absorbing agent, and a weight W0 (g) was measured. Then, from the weights W1 and W0, the centrifuge retention capacity (CRC) (g/g) was calculated according to the following equation.

Centrifuge Retention Capacity(CFC)(g/g)=($W1$(g)−$W0$(g))/(weight(g)of water absorbing agent)−1

<Absorbency Against Pressure of 4.83 kPa (AAP)>

The absorbency against pressure (AAP) represents an absorption capacity at which 0.90 wt % of saline is absorbed for 60 minutes at 4.83 kPa. The AAP is also referred to as absorbency under a pressure of 4.83 kPa. FIG. 1 is a cross sectional view illustrating a measuring apparatus of AAP.

With the use of the measuring apparatus illustrated in FIG. 1, the absorbency against pressure (AAP) was measured. On a bottom of a plastic supporting cylinder 100 having a 60 mm internal diameter, a Stainless metal net 101 of 400 mesh (mesh size of 38 μm) was fusion-bonded. Then, under a condition of a room temperature (20° C. to 25° C.) and 50% RH humidity, 0.900 g of a water absorbing agent was evenly dispersed on the stainless metal net 101. Subsequently, a piston 103 and a load 104 were placed in this order on the water absorbing agent. External diameters of the piston 103 and the load 104 were slightly smaller than 60 mm which was the internal diameter of the supporting cylinder 100, so that there was no gap between the piston and the supporting cylinder, and upward and downward movements of the piston 103 and the load 104 would not be hampered. Note that, the piston 103 and the load 104 were so adjusted as to evenly apply a 4.83 kPa (0.7 psi) load onto the water absorbing agent as a test body 102. Then, a weight Wa (g) of the entire measuring apparatus 10 was measured.

Inside a petri dish 105 having a 150 mm diameter, a glass filter 106 (product of Sougo Rikagaku Glass Seisakusho Co., Ltd.; diameter of fine pores: 100 μm to 120 μm) having a 90 mm diameter was placed. Thereafter, 0.90 wt % saline 108 (at not less than 20° C. but not more than 25° C.) was added until it reached a level of an upper surface of the glass filter 106.

Then, a piece of filter paper 107 (product of Advantec Toyo Kaisha, Ltd.; product name: JIS P3801, No. 2; thickness: 0.26 mm; diameter of retained particles: 5 μm) having a 90 mm diameter was placed thereon, so that an entire surface of the filter paper 107 was wetted. An excess of the 0.90 wt % saline 108 was removed.

A set of the measuring apparatus 10 was placed on the wet filter paper 107. Then, the water absorbing agent was made to absorb the solution for one hour under the load. One hour later, the set of the measuring apparatus 10 was lifted, and a weight Wb (g) thereof was measured. From the weights Wa and Wb, the absorption capacity against pressure of 4.83 kPa (AAP) (g/g) was calculated according to the following equation.

Absorption capacity against pressure of 4.83kPa (AAP)=($Wb$(g)−$Wa$(g))/weight(0.900g)of water absorbing agent)

<Saline Flow Conductivity (SFC)>

Figure 2:
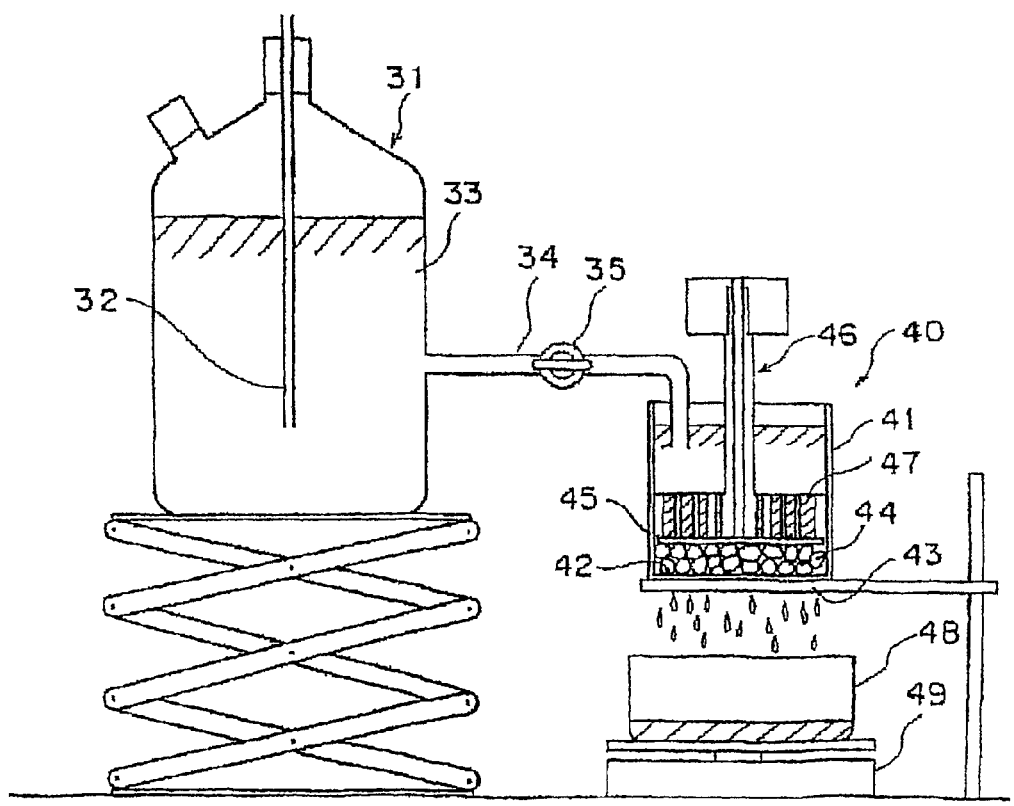
FIG. 2 is a schematic view illustrating a measuring apparatus of SFC, which was used in Examples.

The saline flow conductivity (SFC) is a value indicative of liquid permeability in a case where the water absorbing agent is swollen. As the value of SFC is higher, the liquid permeability is higher. In Examples, a test was carried out on the basis of an SFC test described in U.S. Pat. No. 5,849,405. FIG. 2 is a view schematically illustrating a measuring apparatus of SFC.

In the measurement apparatus illustrated in FIG. 2, a glass tube 32 was inserted into a tank 31, and a lower end of the glass tube 32 was disposed so that 0.69 wt % saline 33 was positioned 5 cm higher than a bottom of the swelling gel 44 in a cell 41. Further, the 0.69 wt % saline 33 contained in the tank 31 was supplied to the cell 41 via an L-shaped tube 34 with a cock. A collecting container 48 for collecting liquid having passed through a gel layer was disposed under the cell 41, and the collecting vessel 48 was placed on a pan scales 49. An inside diameter of the cell 41 was 6 cm, and No. 400 stainless metal net (38 μm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that the water absorbing agent or the swelling gel did not enter into the hole 47. The cell 41 was placed on a table for the cell, and the table's surface which is in contact with the cell 41 was positioned on the stainless metal gauze 43 which did not prevent the liquid from passing through.

A artificial urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of pure water.

By use of the measurement apparatus illustrated in FIG. 2, the water absorbing agent (0.900 g) evenly contained in a container 40 was swollen in the artificial urine (1) under a pressure of 2.07 kPa (0.3 psi) for 60 minutes, so as to obtain the gel 44, and a height of a gel layer of the gel 44 was recorded. Then, the 0.69 wt % saline 33 was made to flow from the tank 31 and to pass through the swelling gel layer at a constant hydrostatic pressure under the pressure of 2.07 kPa (0.3 psi). The SFC test was carried out at room temperature (not less than 20° C. but not more than 25° C.). By using a computer and a scale, an amount of liquid passing through the gel layer at intervals of 20 seconds was recorded for 10 minutes as a time function. A flow rate Fs(T) of the solution passing through the swelling gel 44 (mainly between particles thereof) was determined in terms of g/s by dividing an increasing weight (g) by an increasing time (s). A time in which a constant hydrostatic pressure and a stable flow rate had been obtained was set as "Ts", and only data obtained between "Ts" and a ten-minute interval was used to calculate the flow rate, the flow rate calculated between "Ts" and a ten-minute interval was used to calculate a value of Fs (T=0), i.e., a first flow rate of the solution passing through the gel layer. Fs (T=0) was calculated by extrapolating T=0 from a result obtained by approximating a function indicative of a relationship between Fs (T) and Time.

Saline flow conductivity=$(Fs(t=0) \times Lo)/(\rho \times A \times \Delta P)$= $(Fs(t=0) \times Lo)/139506$ Here, Fs (t=0): a flow rate represented by "g/s"

Lo: a height of the gel layer that is represented by "cm"

$\rho$: a density (1.003 g/cm$^3$) of NaCl solution

A: an area (28.27 cm$^2$) on the upper side of the gel layer of the cell 41

$\Delta P$: a hydrostatic pressure (4920 dyne/cm$^2$) exerted to the gel layer. Further, a unit of SFC value is ($10^{-7} \cdot$cm$^3 \cdot$s$\cdot$g$^{-3}$).

In a case where the hydrostatic pressure does not satisfy the above because the liquid passes through too fast, it is also possible to calculate SFC by changing the value $\Delta P$ to a value calculated from a height of the liquid level the saline.

<Mass Median Particle Size (D50) and Logarithmic Standard Deviation ($\sigma\zeta$) of Particle Size Distribution>

Tests were carried out on the basis of mass median particle size (D50) test and logarithmic standard deviation ($\sigma\zeta$) test described in International Publication No. 2004/69915 pamphlet.

<Ratio of Particles Having Particle Size that Allows the Particles to Pass Through Sieve with 150 μm in Mesh>

Classification was carried out in the same manner as the mass median particle size (D50) and the logarithmic standard deviation ($\sigma\zeta$) of the particle size distribution, so that a ratio of particles (wt %) having a particle size that allowed the particles to pass through a sieve with 150 μm in mesh was calculated from an amount of particles that had passed through the sieve with 150 μm in mesh.

<Solid Content of Water Absorbing Agent>

A ratio of components that are not vaporized at 180° C. in the water absorbing agent is as follows. Further, its relation with moisture content is as follows.

Solid content(wt %)=100−moisture content(wt %)

The solid content was measured in the following manner.

About 1 g of a water absorbing agent (weight W1) was measured and poured into an aluminum cup (weight W0) having a bottom surface of about 5 cm in diameter, and left to stand for 3 hours in a calm dryer at 180° C. so that the water absorbing agent was dried. Thereafter, a weight (W2) of the aluminum cup and the water absorbing agent thus dried was measured, and the solid content was calculated according to the following equation.

Solid content(wt %)=$((W2-W0)/W1) \times 100$

<Amount of Water-Soluble Content (Water Soluble Component)>

184.3 g of 0.90 wt % saline was measured and poured into a 250 ml plastic container having a cover. Into the solution, 1.00 g of the water absorbing agent was added, and the plastic container with the solution and the water absorbing agent was stirred for 16 hours by rotating a stirrer, thereby extracting an extractable content from the resin. The extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured so as to be used as a measurement solution.

First, only the 0.90 wt % saline was titrated by using a 0.1N NaOH solution, until pH of the saline reached 10. Thereafter, the saline was titrated by using a 0.1N HCl solution, until pH of the saline reached 2.7. In this way, blank titration amounts ([bNaOH]ml and [bHCl]ml) were measured.

The same operation was performed with respect to the measurement solution, thereby measuring titration amounts ([NaOH]ml and [HCl]ml).

Thereafter, for example, in a case of a water absorbing agent including a known amount of acrylic acid and its sodium salt as its main component, an amount of a water-soluble content in the water absorbing agent was calculated, in accordance with the following equation, from an average molecular weight of the monomer and the titration amounts obtained by the foregoing operation. In a case of a water absorbing agent including an unknown amount of acrylic acid and its sodium salt, an average molecular weight of the monomer was calculated by using a neutralization ratio calculated by titration.

Water-soluble content(wt %)=0.1×(average molecular weight)×184.3×100×([HCl]−[bHCl])/1000/1.0/50.0

Neutralization ratio(mol %)=(1−([NaOH]−[bNaOH])/ ([HCl]−[bHCl]))×100

EXAMPLES

Reference Example 1

In a reactor formed by attaching a cover to a double-arm type stainless kneader having a capacity of 10 liters and equipped with two sigma type blades and a jacket, a reaction liquid was obtained by dissolving 434.0 g of acrylic acid, 4356.9 g of 37 wt % sodium acrylate aqueous solution, 660.1 g of pure water, and 9.69 g of polyethylene glycol diacrylate (average molecular weight is 523). Next, the reaction liquid was degassed for 20 minutes under an atmosphere of nitrogen gas. Continuously, 16.21 g of 20 wt % sodium persulfate aqueous solution and 23.16 g of 1 wt % L-ascorbic acid aqueous solution were added to the reaction liquid while being stirred, and then polymerization started after approximately 20 seconds. Then, the polymerization was carried out at a temperature in a range of 25° C. to 90° C. while the resultant gel was crushed. A hydrogel cross-linked polymer was taken out 30 minutes after the beginning of the polymerization. The time from when the polymerization started until when the reaction liquid reached the highest temperature was within 15 minutes. The obtained hydrogel (hydrogel cross-linked polymer) was crushed so as to be approximately 5 mm or less in diameter.

The crushed hydrogel cross-linked polymer was spread on a metal net of 50 mesh, and then hot-air dried at 185° C. for 45 minutes. The dried hydrogel was pulverized with a roller mill, and then classified with a JIS standard sieve having a mesh size of 710 μm. Particles passing through the JIS standard sieve were further classified with a JIS standard sieve having a mesh size of 175 μm. Microparticles passing through the JIS standard sieve having a mesh size of 175 μm were excluded, thereby obtaining an irregularly-pulverized water absorbent resin (A) having a mass median particle size (D50) of 350 μm and 0.33 log standard deviation ($\sigma\xi$) of particle-size distribution. The water absorbent resin (A) had a centrifugal retention capacity (CRC) of 34.0 (g/g), and included 9.0 wt % of water-soluble contents and 1.0 wt % of particles having a size with which the particles can pass through a sieve having a mesh size of 150 μm.

A surface-cross-linking agent composed of a liquid prepared by mixing 0.35 pts.wt. of 1,4-butanediol, 0.55 pts.wt. of propylene glycol, 3.0 pts.wt. of deionized water, and 0.1 pts.wt. of sodium persulfate was evenly mixed with 100 pts.wt. of the obtained water absorbing agent (A). The resultant mixture was heated at 212° C. for 35 minutes. Then, obtained particles were pulverized so as to pass through a JIS standard sieve having a mesh size of 710 μm. Water absorbent resin particles (1) each having a cross-linked surface were thus obtained.

Example 1

Added to 100 pts.wt. of the water absorbent resin particles (1) was 2.94 pts.wt. of 33.9 wt % ethanol solution of sodium oleate (dissolved in a solvent prepared by mixing water and ethanol with a mass ratio of 1:1). The addition was carried out while the water absorbent resin particles (1) were stirred so that the solution was evenly mixed. Further added to the resultant mixture was 2.24 pts.wt. of 27.5 wt % aluminium sulfate aqueous solution (Asada Chemical Industry Co., Ltd., 8 wt % in terms of aluminium oxide). The addition was carried out in the aforementioned manner so that the solution was evenly mixed. The obtained mixture was dried by letting stand at 60° C. for 30 minutes with no air flow blown thereto. The dried mixture was passed through a JIS standard sieve having a mesh size of 710 μm. A water absorbing agent (1) was thus obtained.

Example 2

A water absorbing agent was produced in the same way as Example 1, except that the amount of 27.5 wt % aluminium sulfate aqueous solution was changed to 4.48 pts.wt. A water absorbing agent (2) was thus obtained.

Reference Example 2

An aqueous solution was prepared by dissolving 1 g of sodium dodecylbenzenesulfonate in 89 g of deionized water. The aqueous solution was maintained at 90° C. in a 500 ml beaker. While the aqueous solution that was maintained at 90° C. was stirred with a homodisper (at a mixing speed of 2000 rpm), 10 g of stearic acid heated to 90° C. was slowly dropped in the aqueous solution, thereby obtaining an emulsified liquid of stearic acid. The emulsified liquid (liquid temperature of 90° C.) was cooled rapidly down to 10° C., and thereafter warmed immediately to room temperature. A stearic acid-emulsified liquid (A) that is milky white in color was thus obtained.

Example 3

Added to 100 pts.wt. of the water absorbent resin particles (1) was 5 pts.wt. of the stearic acid-emulsified liquid (A) obtained in Reference Example 2. The addition was carried out while the water absorbent resin particles (1) were stirred so that the solution was evenly mixed. Further added to the resultant mixture was 1.67 pts.wt. of 30 wt % polyethylenimine aqueous solution (NIPPON SHOKUBAI CO., LTD. P-1000, number average molecular weight of approximately 70000). The addition was carried out in the aforementioned manner so that the solution was evenly mixed. The obtained mixture was dried by letting stand at 60° C. for 30 minutes with no air flow blown thereto. The dried mixture was passed through a JIS standard sieve having a mesh size of 710 μm. A water absorbing agent (3) was thus obtained.

Example 4

Added to 100 pts.wt. of the water absorbing agent (3) obtained in Example 3 was 0.80 pts.wt. of aluminum sulfate 27 wt % solution (8 wt % in terms of aluminum oxide), 0.134 pts.wt. of sodium lactate 60 wt % solution, and 0.016 pts.wt. of propylene glycol. The addition was carried out while the water absorbing agent (3) was stirred so that the solution was evenly mixed. The obtained mixture was dried by letting stand at 60° C. for 30 minutes with no air flow blown thereto. The dried mixture was pulverized so as to pass through a JIS standard sieve having a mesh size of 710 μm. A water absorbing agent (4) was thus obtained.

Example 5

0.30 pts.wt. of Aerosil® 200 produced by Nippon aerosil co., ltd. was added to and mixed with 100 pts.wt. of the water absorbing agent (2) obtained in Example 2. A water absorbing agent (5) was thus obtained.

Example 6

0.30 pts.wt. of Aerosil® 200 produced by Nippon aerosil co., ltd. was added to and mixed with 100 pts.wt. of the water absorbing agent (3) obtained in Example 3. A water absorbing agent (6) was thus obtained.

Example 7

0.30 pts.wt. of Aerosil® 200 produced by Nippon aerosil co., ltd. was added to and mixed with 100 pts.wt. of the water absorbing agent (4) obtained in Example 4. A water absorbing agent (7) was thus obtained.

Example 8

Evenly mixed with 100 pts.wt. of the water absorbent resin (A) obtained in Reference Example 1 was a surface-cross-linking agent made of a mixture solution including 0.35 pts.wt. of 1,4-butandiol, 0.55 pts.wt. of propylene glycol, 3.0 pts.wt. of pure water, and 0.001 pts.wt. of sodium oleate. Subsequently, the resulting mixture was heated at 212° C. for 35 minutes. After heating, added to 100 pts.wt. of the obtained particles was 2.24 pts.wt. of aluminum sulfate 27.5 wt % solution (8 wt % in terms of aluminum oxide). The addition was carried out while the particles were stirred so that the solution was evenly mixed. The obtained mixture was dried by letting stand at 60° C. for 30 minutes with no air flow blown thereto. The dried mixture was pulverized so as to pass through a JIS standard sieve having a mesh size of 710 μm. A water absorbing agent (8) was thus obtained.

Comparative Example 1

The water absorbent resin particles (1) were provided as a comparative water absorbing agent (1).

Comparative Example 2

Added to 100 pts.wt. of the water absorbent resin particles (1) was 2.94 pts.wt. of 33.9 wt % ethanol solution of sodium oleate. The addition was carried out while the water absorbent resin particles (1) were stirred so that the solution was evenly mixed. The obtained mixture was dried by letting stand at 60° C. for 30 minutes with no air flow blown thereto. The dried mixture was passed through a JIS standard sieve having a mesh size of 710 μm. A comparative water absorbing agent (2) was thus obtained.

Comparative Example 3

Added to 100 pts.wt. of the water absorbent resin particles (1) was 2.24 pts.wt. of 27.5 wt % aluminium sulfate aqueous solution (Asada Chemical Industry Co., Ltd., 8 wt % in terms of aluminium oxide). The addition was carried out while the water absorbent resin particles (1) were stirred so that the solution was evenly mixed. The obtained mixture was dried by letting stand at 60° C. for 30 minutes with no air flow blown thereto. The dried mixture was passed through a JIS standard sieve having a mesh size of 710 μm. A comparative water absorbing agent (3) was thus obtained.

Comparative Example 4

The following experiment was carried out with reference to Example 7 in Japanese Unexamined Patent Publication No. 344103/2005 (Tokukai 2005-344103).

Mixed with 2 pts.wt. of 27.5 wt % aluminium sulfate aqueous solution (Asada Chemical Industry Co., Ltd., 8 wt % in terms of aluminium oxide) was 1 pts.wt. of 50% sodium lactate aqueous solution. As a result, a transparent solution that is evenly mixed was obtained. While 3 pts.wt. of the transparent solution was stirred, 100 pts.wt. of the water absorbent resin particles (1) were added thereto so as to be evenly mixed in the solution. Then, the mixture was dried at 60° C. for 1 hour. The dried mixture was passed through a JIS standard sieve having a mesh size of 710 μm. A comparative water absorbing agent (4) was thus obtained.

Comparative Example 5

Added to 100 pts.wt. of the water absorbent resin particles (1) was 5 pts.wt. of the stearic acid-emulsified liquid (A) obtained in Reference Example 2. The addition was carried out while the water absorbent resin particles (1) were stirred so that the solution was evenly mixed. The obtained mixture was dried by letting stand at 60° C. for 30 minutes with no air flow blown thereto. The dried mixture was passed through a JIS standard sieve having a mesh size of 710 μm. A comparative water absorbing agent (5) was thus obtained.

Comparative Example 6

Added to 100 pts.wt. of the water absorbent resin particles (1) was 1.67 pts.wt. of 30 wt % polyethylenimine aqueous solution (NIPPON SHOKUBAI CO., LTD. P-1000, number average molecular weight of approximately 70000). The addition was carried out while the water absorbent resin particles (1) were stirred so that the solution was evenly mixed. The obtained mixture was dried by letting stand at 60° C. for 30 minutes with no air flow blown thereto. The dried mixture was passed through a JIS standard sieve having a mesh size of 710 μm. A comparative water absorbing agent (6) was thus obtained.

Comparative Example 7

Added to 100 pts.wt. of the water absorbent resin particles (1) was 1 pts.wt. of powdered aluminium monostearate (structural formula: Al(OH)2(C17H35COO)). The addition was carried out while the water absorbent resin particles (1) were stirred so that the solution was evenly mixed. The obtained mixture was dried by letting stand at 60° C. for 30 minutes with no air flow blown thereto. The dried mixture was passed through a JIS standard sieve having a mesh size of 710 μm. A comparative water absorbing agent (7) was thus obtained.

CRC, SFC, and AAP measured in each of water absorbing agents (1) through (3) and in comparative water absorbing agents (1) through (7) were shown in Table 1.

TABLE 1

| | | ORGANIC ACID (SALT) | WATER-SOLUBLE POLYVALENT CATION | CRC (g/g) | SFC ($10^{-7} cm^3 sg^{-1}$) | AAP (4.83 kPa) (g/g) |
|---|---|---|---|---|---|---|
| EX. 1 | WATER ABSORBING AGENT (1) | SODIUM OLEATE | ALUMINIUM SULFATE | 25.6 | 221 | 22.3 |
| EX. 2 | WATER ABSORBING AGENT (2) | SODIUM OLEATE | ALUMINIUM SULFATE | 25.1 | 235 | 21.1 |
| EX. 3 | WATER ABSORBING AGENT (3) | STEARIC ACID | POLYETHYLEN-IMINE | 25.8 | 210 | 21.8 |
| EX. 4 | WATER ABSORBING AGENT (4) | STEARIC ACID | POLYETHYLEN-IMINE ALUMINIUM SULFATE | 25.7 | 215 | 21.5 |
| EX. 5 | WATER ABSORBING AGENT (5) | SODIUM OLEATE | ALUMINIUM SULFATE (+AMORPHOUS SILICA) | 25.6 | 230 | 22.0 |
| EX. 6 | WATER ABSORBING AGENT (6) | STEARIC ACID | POLYETHYLEN-IMINE (+AMORPHOUS SILICA) | 25.1 | 242 | 20.9 |
| EX. 7 | WATER ABSORBING AGENT (7) | STEARIC ACID | POLYETHYLEN-IMINE ALUMINIUM SULFATE | 25.7 | 219 | 21.5 |

TABLE 1-continued

| | | ORGANIC ACID (SALT) | WATER-SOLUBLE POLYVALENT CATION | CRC (g/g) | SFC ($10^{-7}cm^3sg^{-1}$) | AAP (4.83 kPa) (g/g) |
|---|---|---|---|---|---|---|
| EX. 8 | WATER ABSORBING AGENT (8) | SODIUM OLEATE | (+AMORPHOUS SILICA) ALUMINIUM SULFATE | 25.5 | 200 | 22.9 |
| COM. EX. 1 | COM. WATER ABSORBING AGENT (1) | NO | NO | 26.5 | 96 | 24.5 |
| COM. EX. 2 | COM. WATER ABSORBING AGENT (2) | SODIUM OLEATE | NO | 25.7 | 90 | 23.5 |
| COM. EX. 3 | COM. WATER ABSORBING AGENT (3) | NO | ALUMINIUM SULFATE | 25.5 | 153 | 22.9 |
| COM. EX. 4 | COM. WATER ABSORBING AGENT (4) | SODIUM LACTATE | ALUMINIUM SULFATE | 25.1 | 166 | 22.3 |
| COM. EX. 5 | COM. WATER ABSORBING AGENT (5) | STEARIC ACID | NO | 25.5 | 81 | 23.3 |
| COM. EX. 6 | COM. WATER ABSORBING AGENT (6) | NO | POLYETHYLEN-IMINE | 25.9 | 149 | 22.9 |
| COM. EX. 7 | COM. WATER ABSORBING AGENT (7) | ALUMINIUM MONO-STEARATE | NO | 26.4 | 92 | 24.0 |

Abbreviation: EX. stands for EXAMPLE
COM. EX. stands for COMPARATIVE EXAMPLE
COM. WATER ABSORBING AGENT means for COMPARATIVE WATER ABSORBING AGENT As shown in Table 1, water absorbing agents obtained in Examples of the present invention exhibited a high absorbing capacity (centrifugal retention capacity (CRC)) and an extremely high liquid-permeability under pressure (saline flow conductivity (SFC)). It was also indicated that the above-mentioned effects could be attained in case where an organic acid and/or salt thereof having carbon number of 10 or more and not more than 30 in its molecule and water-soluble polyvalent cation exist together on a surface of each of water absorbent resin particles.

Example 9

Evenly mixed with 100 pts.wt. of the water absorbent resin (A) obtained in Reference Example 1 was a surface-cross-linking agent made of a mixture solution including 0.35 pts.wt. of 1,4-butandiol, 0.55 pts.wt. of propylene glycol, and 3.0 pts.wt. of pure water. Subsequently, the resulting mixture was heated at 212° C. for 25 minutes. Thereafter, the obtained mixture was pulverized so as to pass through a JIS standard sieve having a mesh size of 710 µm. Surface-crosslinked water absorbent resin particles (2) were thus obtained. The surface-crosslinked water absorbent resin particles (2) were subjected to the same process as Example 1. A water absorbing agent (9) was thus obtained.

Comparative Example 8

The water absorbent resin particles (2) were regarded as a comparative water absorbing agent (8).

Comparative Example 9

The water absorbent resin particles (2) obtained in Example 9 were subjected to the same process as Comparative Example 2. A comparative water absorbing agent (9) was thus obtained.

Comparative Example 10

The water absorbent resin particles (2) obtained in Example 10 were subjected to the same process as Comparative Example 3. A comparative water absorbing agent (10) was thus obtained.

CRC, SFC, and AAP measured in each of the water absorbing agent (9) and in the comparative water absorbing agents (8) through (10) were shown in Table 2.

TABLE 2

| | | ORGANIC ACID (SALT) | WATER-SOLUBLE POLYVALENT CATION | CRC (g/g) | SFC ($10^{-7}cm^3sg^{-1}$) | AAP (4.83 kPa) (g/g) |
|---|---|---|---|---|---|---|
| EX. 9 | WATER ABSORBING AGENT (9) | SODIUM OLEATE | ALUMINIUM SULFATE | 28.9 | 103 | 23.4 |
| COM. EX. 8 | COM. WATER ABSORBING AGENT (8) | NO | NO | 29.2 | 51 | 25.1 |

TABLE 2-continued

| | | ORGANIC ACID (SALT) | WATER-SOLUBLE POLYVALENT CATION | CRC (g/g) | SFC ($10^{-7}cm^3sg^{-1}$) | AAP (4.83 kPa) (g/g) |
|---|---|---|---|---|---|---|
| COM. EX. 9 | COM. WATER ABSORBING AGENT (9) | SODIUM OLEATE | NO | 29.0 | 50 | 23.6 |
| COM. EX. 10 | COM. WATER ABSORBING AGENT (10) | NO | ALUMINIUM SULFATE | 28.9 | 75 | 23.5 |

Abbreviation: EX. stands for EXAMPLE
COM. EX. stands for COMPARATIVE EXAMPLE
COM. WATER ABSORBING AGENT means for COMPARATIVE WATER ABSOBING AGENT As shown in Table 2, the water absorbing agent obtained in Example 9 of the present invention exhibited a high absorbing capacity (centrifugal retention capacity (CRC)) and an extremely high liquid-permeability under pressure (saline flow conductivity (SFC)), compared with the water absorbing agents obtained in Comparative Examples 8 through 10. It was also indicated that the above-mentioned effects could be attained in case where an organic acid and/or salt thereof having carbon number of 10 or more and not more than 30 in its molecule and water-soluble polyvalent cation exist together on a surface of each of water absorbent resin particles.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Industrial Applicability

A water absorbing agent according to the present invention, and a water absorbing agent obtained by a method according to the present invention for producing the water absorbing agent are excellent in balance between liquid permeability under load and absorption capacity. Thus, they can be used for water absorbing or moisture holding agents for various uses.

For example, the water absorbing agent are applicable to: water absorbing or moisture holding agents for disposable diapers, sanitary napkins, incontinent pads, medical pads, and the like; agricultural/horticultural water retaining agents such as replacement of bog moss, soil conditioner, water retaining agent, agricultural chemical effect sustaining agents; construction water retaining agent such as anti-dew agent for interior walls, cement additive; release controller; cold insulator; disposable body warmer; sludge coagulator; food freshness keeping materials; ion exchange column materials; dehydrating agent for sludge or oil; drying agents, moisture adjusting materials; and the like.

Moreover, the water absorbing agent according to the present invention is especially suitable for use in sanitary materials for absorbing feces, urine, or blood, such as disposable diaper, sanitary napkins, and the like.

The invention claimed is:

1. A water absorbing agent, comprising:
water absorbent resin particles;
an organic acid and/or salt thereof having carbon number of 10 or more and not more than 30 in its molecule; and
a water-soluble polyvalent cation.

2. The water absorbing agent as set forth in claim 1, wherein the organic acid and/or salt thereof, and the water-soluble polyvalent cation exist on a surface of each of the water absorbent resin particles.

3. The water absorbing agent as set forth in claim 1, wherein the organic acid and/or salt thereof has a hydrocarbon chain having carbon number of 9 or more in its molecule.

4. The water absorbing agent as set forth in claim 1, wherein the surface of the water absorbent resin particle is crosslinked.

5. The water absorbing agent as set forth in claim 1, wherein an amount of the organic acid and/or salt thereof ranges from 0.0001 to 5 mass % relative to an entire amount of the water absorbing agent.

6. The water absorbing agent as set forth in claim 1, wherein an amount of the water-soluble polyvalent cation ranges from 0.001 to 5 mass % relative to an entire amount of the water absorbing agent.

7. The water absorbing agent as set forth in claim 1, wherein the organic acid and/or salt thereof is a compound containing a carboxyl group.

8. The water absorbing agent as set forth in claim 1, wherein the salt is made of organic acid and univalent cation.

9. The water absorbing agent as set forth in claim 1, wherein the water-soluble polyvalent cation is a water-soluble polyvalent metal salt.

10. The water absorbing agent as set forth in claim 1, wherein the water-soluble polyvalent cation is a water-soluble cationic polymer compound.

11. A method for producing a water absorbing agent including water absorbent resin particles, an organic acid and/or salt thereof having carbon number of 10 or more and not more than 30 in its molecule, and a water-soluble polyvalent cation,
said method comprising the step (i) of mixing the water absorbent resin particles, the organic acid and/or salt thereof having carbon number of 10 or more and not more than 30 in its molecule, and the water-soluble polyvalent cation with one another.

12. The method as set forth in claim 11, further comprising the step (ii) of cross-linking a surface of each of the water absorbent resin particles with a surface cross-linking agent.

13. The method as set forth in claim 12, wherein the step (i) is carried out during the step (ii) and/or after the step (ii).

14. The method as set forth in claim 11, wherein the step (i) is such that the organic acid and/or salt thereof having carbon number of 10 or more and not more than 30 in its molecule is mixed with the water absorbent resin particles at the same time as or before addition of the water-soluble polyvalent cation.

15. The method as set forth in claim 11, wherein in the step (i), an aqueous solution of the water-soluble polyvalent cation is mixed in.

16. The method as set forth in claim 11, wherein the salt of the organic acid is made of the organic acid and univalent cation.

\* \* \* \* \*